US011464204B2

(12) United States Patent
van Kilsdonk et al.

(10) Patent No.: US 11,464,204 B2
(45) Date of Patent: Oct. 11, 2022

(54) LIVE INSECTS TRANSPORT DEVICE

(71) Applicant: Protix B.V., Dongen (NL)

(72) Inventors: Jaap van Kilsdonk, Veldhoven (NL); Eric Holland Schmitt, Antwerp (BE); Ralf Henricus Wilhelmina Jacobs, Eindhoven (NL); Henricus Petrus Johannes Simons, Den Bosch (NL); Maurits Petrus Maria Jansen, Bavel (NL)

(73) Assignee: Protix B.V., Dongen (NL)

( * ) Notice: Subject to any disclaimer, the term of this patent is extended or adjusted under 35 U.S.C. 154(b) by 77 days.

(21) Appl. No.: 16/954,534

(22) PCT Filed: Dec. 21, 2018

(86) PCT No.: PCT/NL2018/050867
§ 371 (c)(1),
(2) Date: Jun. 17, 2020

(87) PCT Pub. No.: WO2019/125162
PCT Pub. Date: Jun. 27, 2019

(65) Prior Publication Data
US 2021/0076637 A1 Mar. 18, 2021

(30) Foreign Application Priority Data

Dec. 22, 2017 (NL) .................................... 2020153
Nov. 23, 2018 (NL) .................................... 2022057

(51) Int. Cl.
*A01K 1/08* (2006.01)
*A01K 1/00* (2006.01)
*A01K 67/033* (2006.01)

(52) U.S. Cl.
CPC .............. *A01K 1/08* (2013.01); *A01K 1/0047* (2013.01); *A01K 67/033* (2013.01)

(58) Field of Classification Search
CPC ....... A01K 1/08; A01K 1/0047; A01K 67/033
See application file for complete search history.

(56) References Cited

U.S. PATENT DOCUMENTS 3,223,237 A * 12/1965 Harrod, Jr. ........... A01K 67/033
209/2
3,893,420 A * 7/1975 Andreev ............... A01K 67/033
119/6.6

(Continued)

FOREIGN PATENT DOCUMENTS

RU       2336696 C1 * 10/2008 ........... A01K 67/033
RU       2336696 C1    10/2008
WO       WO-2021007541 A1 * 1/2021 ............ A01K 29/00

*Primary Examiner* — Monica L Barlow
*Assistant Examiner* — Aaron M Rodziwicz
(74) *Attorney, Agent, or Firm* — N.V. Nederlandsch Octrooibureau

(57) ABSTRACT

The invention relates to a device for use in large-scale industrial insect farming. More in particular, the invention relates to a live insects transport device for transporting live insects from a first location to a predetermined second location, the live insects transport device comprising a fluid guiding unit, a fluid discharge member and a feeder arrangement, wherein the live insects transport device is configured to receive live insects such as freshly hatched neonate larvae, for example of black soldier fly, wherein the live insects are taken up in a laminar flow of fluid and while in said fluid are transported to a predetermined location in the live insects transport device. Furthermore, the invention relates to the use of the device in industrial insect farming, such as large-scale farming of black soldier flies, and the invention relates to a method of dosing live insects, wherein preferably live insects are doses which are essentially of the same age, such as freshly hatched neonate larvae.

22 Claims, 13 Drawing Sheets

(56) References Cited

U.S. PATENT DOCUMENTS

| | | | | |
|---|---|---|---|---|
| 5,594,654 | A * | 1/1997 | Shuman | A01K 67/033 700/213 |
| 5,927,004 | A * | 7/1999 | Stocker | A01K 67/033 47/58.1 R |
| 8,602,837 | B1 * | 12/2013 | Allan | A01K 67/033 449/1 |
| 10,842,138 | B1 * | 11/2020 | Lolley | A01K 29/005 |
| 2013/0319334 | A1 * | 12/2013 | Newton | A01K 29/00 119/6.5 |
| 2014/0020630 | A1 * | 1/2014 | Courtright | A01K 67/033 119/6.6 |
| 2015/0008163 | A1 * | 1/2015 | Nimmo | B07B 13/04 209/17 |
| 2015/0122182 | A1 * | 5/2015 | Aldana | A01K 67/033 119/6.6 |
| 2015/0296760 | A1 * | 10/2015 | Perednia | A01K 67/033 119/6.5 |
| 2017/0202191 | A1 * | 7/2017 | Marchant | F21V 7/22 |
| 2019/0191678 | A1 * | 6/2019 | Alrayya | A23K 50/90 |
| 2019/0387704 | A1 * | 12/2019 | Hall | A01K 67/033 |
| 2020/0008408 | A1 * | 1/2020 | Jansen | F28F 27/00 |
| 2020/0375161 | A1 * | 12/2020 | Emery | B07B 1/24 |

* cited by examiner

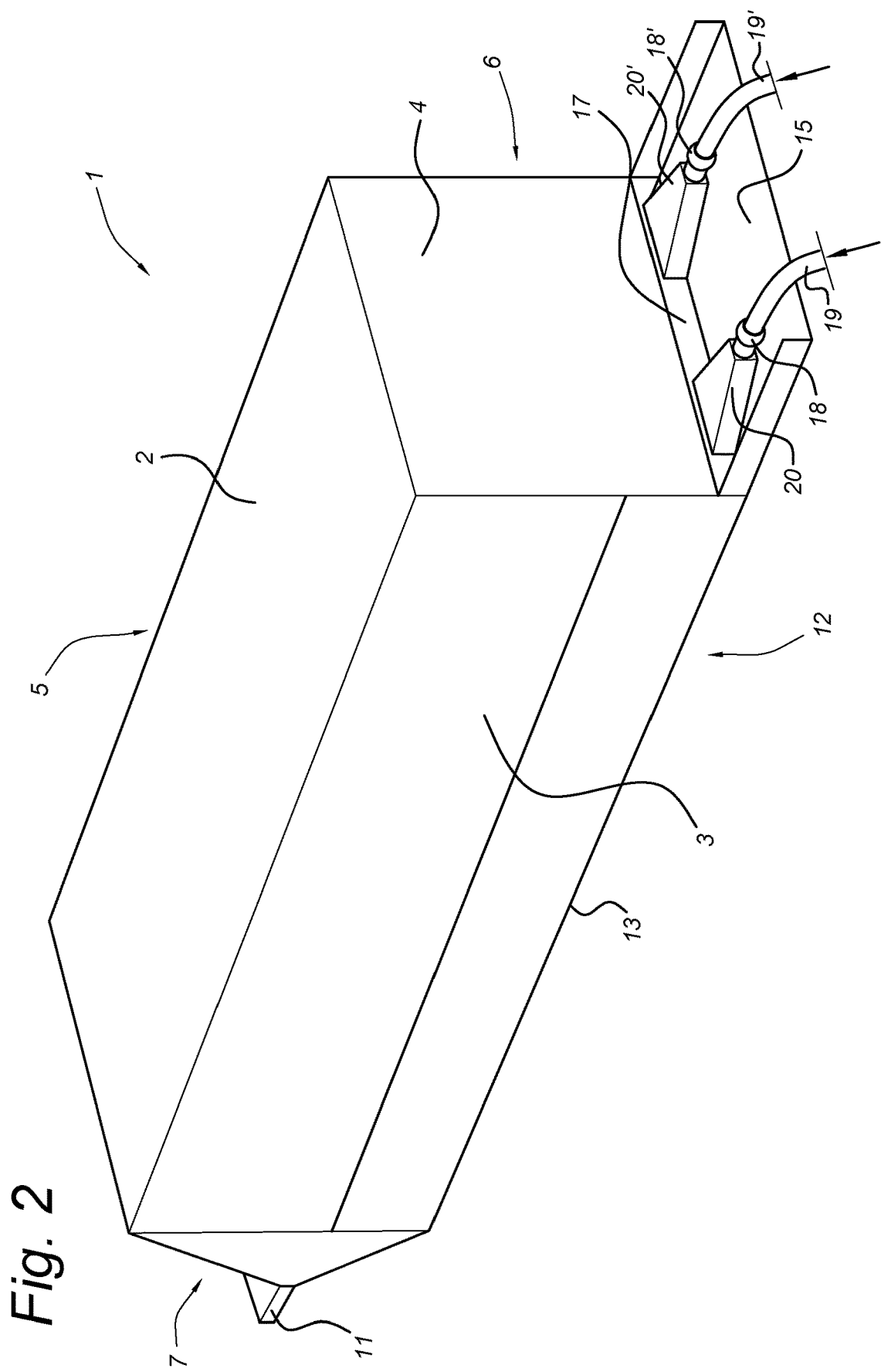

LIVE INSECTS TRANSPORT DEVICE

TECHNOLOGICAL FIELD OF THE INVENTION

The invention relates to a device for use in large-scale industrial insect farming. More in particular, the invention relates to a live insects transport device for transporting live insects from a first location to a predetermined second location, the live insects transport device comprising a fluid guiding unit, a fluid discharge member and a feeder arrangement, wherein the live insects transport device is configured to receive live insects such as freshly hatched neonate larvae, for example of black soldier fly, wherein the live insects are taken up in a laminar flow of fluid and while in said fluid are transported to a predetermined location in the live insects transport device. Furthermore, the invention relates to the use of the device in industrial insect farming, such as large-scale farming of black soldier flies, and the invention relates to a method of dosing live insects, wherein preferably live insects are doses which are essentially of the same age, such as freshly hatched neonate larvae.

BACKGROUND OF THE INVENTION

Insects are considered one of the most promising means for protein and for organic residual recovery. Prominent examples of species proposed for the indicated applications include the black soldier fly (*Hermetia illucens*), the house fly (*Musca domestica*), and the mealworm (*Tenebrio molitor* L.).

Methods improving the efficiency of insect farming relating to improvements in farming colonies of insects having essentially the same age are particularly valuable for large scale production. This, because of the batch wise nature of the insect farming steps that should be performed in order to be able to arrive at an economically viable scale. Since aiming for large-scale insect farming is a desired industrial activity that involves live animals, synchronization of the age of insects in a colony, which are then essentially in the same stage of the insect life cycle, would contribute to efficient use of farming facilities and would aid in achieving predictable production volumes. Furthermore, synchronization and steering of the age of batches of insect colonies which are in subsequent insect stages would further contribute to efficient use of farming facilities. However, methods and means for efficaciously and beneficially interfering in the life cycle of insects forming a colony, such that within the colony the insects essentially have the same age to the benefit of industrial-scale insect farming, are at present not available in the art.

U.S. Pat. No. 3,893,420 A discloses a method of mass-producing parasitic insects by infecting crop seeds with eggs of a host insect; collecting the imagoes of the host insect where their eggs are accumulated and attaching the imago eggs to a standard carrier; subjecting the eggs to climatic conditions and infecting the imago eggs with parasitic insects under climatic, natural conditions through phototaxis for conditioning the parasitic insect eggs so they are available for use in effective biological control material for controlling agricultural pests.

SUMMARY OF THE INVENTION

It is a first goal of the present invention to take away the above mentioned disadvantages, or at least to provide a useful alternative to the state of the art.

It is an object of the current invention to provide a means for automated and efficient transport of live insects such as live neonate larvae, preferably directly after the insects hatched.

It is an object of the current invention to provide a means for automated and efficient transport of live insects such as live neonate larvae, wherein the automated transport means does not do harm to the live insects and does not injure or even kill the live insects during transportation or thereafter as a result of the transportation with said means for transport of live insects.

It is another or alternative object to provide a means for automated and efficient transport of live insects such as live neonate larvae from the location where the insects hatch to a location where the live insects are countable and preferably dosable and/or analyzable with regard to the age of the live insects transported by using the means for automated and efficient transport of live insects.

Furthermore, it is yet another or alternative object to transport live insects without imposing any harm to said insects and to transport live insects efficaciously from a first location to a predetermined second location, with minimal losses of insects by fall-out during transportation.

At least one of the above objectives is achieved by a live insects transport device for transporting live insects from a first location to a predetermined second location, the live insects transport device comprising a fluid guiding unit, a first fluid discharge member and a feeder arrangement, wherein the live insects transport device is configured to receive live insects such as live freshly hatched neonate larvae, for example of black soldier fly, wherein the live insects are taken up in a laminar flow of fluid and while in said fluid are transported to a predetermined location in the live insects transport device.

The objective of keeping transported insects viable, alive and uninjured during transportation by the live insects transport device of the invention, or thereafter as a consequence of the transportation by said live insects transport device of the invention, is achieved by applying the live insects transport device, according to the invention. That is to say, amongst other defining tests, the inventor established that live insects transported by the live insects transport device of the invention are equally viable as live insects not transported by the live insects transport device of the invention and otherwise being treated equally. No signs of any injury or increased number of death insects due to subjecting live insects to transportation by the live insects transport device of the invention was indicated, when compared to similar live insects not subjected to the transportation by using the live insects transport device of the invention. Tests were performed with freshly hatched neonate larvae of black soldier fly.

As said, the live insects transport device of the invention transports live insects to a predetermined location when in operation. At such predetermined location in the live insects transport device, a tunable outflow of live insects is provided for, with regard to the number of live insects exiting the live insect transport device per time unit, e.g. per second or per minute, and/or with regard to the number of live insects exiting the live insects transport device per volume of fluid in the laminar flow of fluid, according to the invention. Herewith, the live insects transport device of the invention provides for a means to deliver live insects per time unit and/or per volume in a manner that such transported live insects are for example subsequently countable after exiting the device of the invention and/or are dosable by for example receiving an amount of live insects in a receptacle for a certain period of time in which the live insect transport device of the invention is in operation, and/or receiving the amount of live insects in a certain volume of fluid in the laminar flow of fluid exiting the device of the invention when in operation, according to the invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The embodiments of the invention described herein can operate in combination and cooperation, unless specified otherwise.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

A first aspect of the current invention relates to a live insects transport device, in particular a live insect larvae transport device, comprising:

a fluid guiding unit comprising a distal end and a proximal end, and at least one longitudinal fluid guiding member comprising a distal end and a proximal end, wherein the distal end of the fluid guiding member is arranged at the distal end of the fluid guiding unit and wherein the proximal end of the fluid guiding member is directed toward the proximal end of the fluid guiding unit, wherein the at least one fluid guiding member further comprises a smooth top surface extending from the distal end to the proximal end of the fluid guiding member, the top surface comprising a live insects receiving portion between the distal end and proximal end of the at least one fluid guiding member, and wherein the fluid guiding member is tilted at an angle α relative to the horizontal;

a first fluid discharge member located at the distal end of the fluid guiding unit and being configured to connect to a source of fluid, wherein the first fluid discharge member is further configured to provide a first laminar flow of fluid over the top surface of the at least one fluid guiding member from the distal end to the proximal end thereof during operation of the transport device; and wherein the transport device further comprises a feeder arrangement located above the live insects receiving portion of the top surface of the fluid guiding unit, wherein the feeder arrangement is configured to receive at least one reservoir for releasing live insects above the live insects receiving portion, wherein the live insect larvae transport device further comprises a casing covering the fluid guiding unit and wherein the feeder arrangement further comprises a temperature control unit for controlling the temperature at the inner side of the casing and/or further comprising a unit for controlling relative air humidity at the inner side of the casing.

When in operation, the live insect transport device of the invention provides a tunable supply of live insects in the laminar flow of fluid at a predetermined location in the live insects transport device, such as for example at the downstream location of the laminar flow of fluid, i.e. the proximal end of the fluid guiding member. As described, this way, a stream of live insects in a laminar flow of fluid is provided that is for example suitable for subsequently feeding for example a live insect analysis arrangement, according to the invention, upon exiting of the live insects from the device of the invention. Typically, a live insect analysis arrangement is an imaging device comprising analysis software, which is capable of imaging live insects exiting the life insects transport device of the invention and passing through an imaging zone, and capable of providing instant feedback on for example the size and/or shape and/or color and/or weight of the transported live insects. This provides a manner of sorting and/or dosing live insects transported by the transport device of the invention. For example, transported live insects are collected in a receptacle when a certain predetermined cut-off for a parameter value such as volume, size, etc., is determined, and transported live insects are not collected for example for further farming, when said certain predetermined cut-off for a parameter value is not reached or exceeded, as the case may be, according to the invention. For example, sorting live insects based on a predetermined size, or average size with a certain size tolerance, or size window, improves the synchronization of insect age within a colony consisting of insects having such predetermined size, etc., according to the invention. Use of the live insects transport device of the invention thus contributes to improved farming performance by contributing to establishment of insect colonies comprising insects with less difference in age than what is obtainable when applying current methods of (small scale) insect farming.

In one embodiment, the live insects transport device according to the invention is a device wherein the at least one fluid guiding member has a length in the longitudinal direction of between 10 cm and 200 cm, preferably between 20 cm and 140 cm, more preferably between 25 cm and 120 cm, most preferably about 25 cm to 50 cm.

In one embodiment, the live insects transport device according to the invention is a device wherein said transport device comprises at most one longitudinal fluid guiding member.

Large scale insect farming implying an industrial scale providing for an output of for example insect derived proteins, amino-acids, oil, lipids, fat, etc., which is economically feasible, is supported by the use of the live insects transport device of the invention, said device having certain minimal dimensions relating to minimal turnover of transported live insects. It has been established by the current inventors that a live insect transport device comprising a fluid guiding member with a length in the longitudinal direction of between 10 cm and 200 cm, such as about 100 cm to 150 cm or such as about 60 cm to 80 cm provides for the top surface comprising a live insects receiving portion between the distal end and proximal end of the at least one fluid guiding member, wherein said live insects receiving portion has a size suitable for receiving an amount of live insects in the fluid of the laminar flow, which is sufficient and enough for transporting numbers of live insects suitable for farming of the insects at the desired large scale, according to the invention.

In one embodiment, the live insects transport device according to the invention is a device wherein said transport device comprises at least two imbricatedly coupled longitudinal fluid guiding members, the fluid guiding members being imbricatedly coupled with a coupler located at the proximal end of a first fluid guiding member and the distal end of a second fluid guiding member. Preferred is a live insects transport device comprising between two to six longitudinal fluid guiding members, more preferred the live insects transport device comprises between three to four longitudinal fluid guiding members, according to the invention. The live insects transport device comprising for example three longitudinal fluid guiding members encompasses a live insects receiving portion spanning a length of between about 75 cm and 800 cm, according to the invention, such as between about 120 cm and 200 cm. With such a size of the live insects receiving portion, space for positioning up to about 800 reservoirs for releasing live insects above said live insects receiving portion in the feeder arrangement is available, for example in two rows of about 400 reservoirs, each. For example, about a hundred reservoirs or about 128 reservoirs are positioned in the feeder arrangement, in two rows of fifty or 64 reservoirs or in a single row of reservoirs. Preferred is a live insects receiving portion spanning a length of between about 90 cm and 160 cm, according to the invention, which provides sufficient space for positioning up to between about 34 reservoirs and 68 reservoirs for releasing live insects above said live insects receiving portion in the feeder arrangement, for example in two rows of about 34 reservoirs, each, or in a single row of 34 reservoirs or 68 reservoirs, according to the invention. These numbers of reservoirs are configured to contain numbers of live insects for release in the live insects receiving portion of the live insects transport device of the invention, which are sufficiently high as to provide for a stream of transported live insects during a sufficiently long period of time, e.g. 1 hour to 4 days, preferably 3 hours to 3 days, more preferably between 12 hours and 60 hours, most preferably between 16 hours and 48 hours, in order to support large scale insect farming. For example, according to the invention, 30 to 70 reservoirs are positioned in the feeder arrangement of the live insect transport device of the invention, for example for a period of releasing live insects into the laminar flow of fluid during about 48 hours, when operating the transport device, according to the invention. Typically, for example a reservoir containing insect eggs contains between about 10.000 and 500.000 eggs, i.e. live insects, preferably between about 30.000 and 100.000 eggs. Methods improving the efficiency of egg collection from insects such as black soldier fly in a reservoir suitably for application in the live insect transportation device of the invention are particularly valuable for large scale production because the enormous quantity, delicacy, small size and stickiness of eggs. Therefore, it is beneficial to collect insect eggs in a specific location since this simplifies collection operations and allows for efficient subsequent handlings, i.e. hatching while positioned above the live insects receiving section of the transport device of the invention. In the event that the location is a device designed to collect eggs, it will henceforth be referred to as an "ovisite" throughout this application. A preferred reservoir for positioning in the feeder arrangement of the live insect transport device of the invention is an ovisite of between about 15 cm and 60 cm (width) times between about 10 cm and 40 cm (height) times between about 0.6 cm and 2.4 cm (depth), such as an ovisite of about 30 cm (width) times about 20 cm (height) times about 1.2 cm (depth). A preferred ovisite for use in the live insects transport device of the invention when in operation, is an ovisite with honeycomb architecture comprising hexagonal openings, such as a cardboard honeycomb according to the invention. Such cardboard honeycomb comprises sufficient and enough space for bearing a number of live insects, i.e. insect eggs, which is sufficiently high to be able to release a suitable quantity of live insects into the laminar flow of fluid in the live insects transport device.

With a number of reservoirs of between 25 and 100, such as between 34 and 68, or such as about 32 or 64 reservoirs, the reservoirs being honeycombs such as polymer or cardboard honeycombs comprising insect eggs, such as those from black soldier fly, the live insect transport device of the invention is operable for 1 to 3 days, preferably about 2 days, with regard to the number of live insects, here freshly hatched neonate larvae such as those from black soldier fly, exiting the transport device and becoming available for subsequent required steps of insect farming, i.e. culturing in a suitable substrate, according to the invention. For example, the reservoirs applied in the live insect transport device of the invention are reservoirs such as honeycombs, which are typically ovisites of about 2 cm×22 cm×33 cm, that have been located in an adult insect cage comprising about 1.000 to 30.000 gravid female insects, such as about 4.000 gravid insects, such as black soldier flies, for a period of between 12 hours and 72 hours such as for about 24-48 hours, such that those numbers of gravid insects have laid eggs for this indicated period of time. These ovisites filled with insect eggs comprise numbers of live insects enough for releasing sufficient hatched neonate larvae into the live insect receiving section and then into the laminar flow of fluid of the live insect transport device of the invention while in operation, according to the invention. For example, said 32 to 64 ovisites then encompass by estimation between 320.000 eggs and 3.2 million eggs, typically about 1.5 million eggs such as those from black soldier flies for example having an egg to egg age difference of two days or less.

One of the various benefits provided with the live insects transport device of the invention is the possibility to collect neonate larvae of insects which larvae have a narrow window of difference in age. "Narrow" in the context of this synchronization of age of a batch of live insects is to be understood as a maximum age difference between live insects in a batch of live insects transported by the live insect transport device of the invention of at most 2 hours, and typically less than 1 hour, such as for example between 5 minutes and 45 minutes. A "batch" is here defined as a number of live insects that has been transported with the live insects transport device of the invention and that are isolated from the laminar flow of fluid after exiting of the transported live insects out of the transport device of the invention, the number of transported live insects in a batch being defined by the time period of collecting transported live insects and/or the number of transported live insects retrieved from a certain volume of fluid exiting the transport device. Typically, a batch of transported live insects is collected in a receptacle positioned downstream from the laminar flow of fluid exiting the live insects transport device of the invention. Typically, according to the invention, a batch of transported live insects, such as freshly hatched neonate larvae, such as black soldier fly larvae, exited the live insects transport device of the invention, encompasses between 3.000 live insects and 300.000 live insects, preferably between 5.000 and 100.000 live insects, such as about 40.000 neonate larvae, e.g. of black soldier fly, according to the invention. It is thus due to the current invention that batches are provided of sufficiently high numbers of transported live insects, such as freshly hatched neonate larvae, such as black soldier fly larvae, wherein the individual live insects in a batch have a synchronized age that is tunable with a predetermined range. For example, a batch of transported live insects is obtainable that encompasses about 50.000 live insects having an age difference of less than one hour, or that encompasses about 150.000 live insects having an age difference of between 5 minutes and 30 minutes, according to the invention.

It is one of the many benefits achieved with the live insect transport devices of the invention that the transport device is particularly suitable for transportation of live neonate larvae of the black soldier fly, which larvae have a body diameter of between 1 mm and 4 mm and a body length which ranges between 5 mm and 12 mm.

A further benefit provided by the live insects transport device of the invention is the possibility to automate the preparing of batches of transported live insects having a synchronized age within a predetermined time window of for example between 2 minutes and 4 hours, such that for a time period of for example two days the transport device of the invention delivers amounts of transported live insects enough for, for example, providing between 2 and 15 batches of live insects per hour, each batch encompassing for example between 1.000 and 600.000 live insects, such as about 400.000 live insects or about 80.000 live insects, e.g. neonate larvae, the transported live insects in each batch having a maximum age difference of less than 3 hours, such as for example between 3 minutes and 2 hours, or between 6 minutes and 1 hour, according to the invention. These production volumes with regard to the number of batches, the amount of live insect per batch and the synchronized age of live insects in each batch, are suitable for insect farming at a scale required for profitably running a business. That is to say, by applying the live insects transport device of the invention, the number of output batches comprising the indicated numbers of live insects at an insect age within the relatively small window of ages, i.e. batches of live insects with selected numbers of insects having a synchronized age within a predetermined time window, is sufficient and suitable for running an insect farm in a manner that farming equipment has a run time higher than run times that would be reachable without application of the live insect transport device of the invention. It is due to the inventors that now a transport device has become available that makes it possible to provide a predetermined number of colonies of live insects per time unit, e.g. per day, of a predetermined colony size in numbers of live insects, and of an average age within a predetermined time window, such that insect rearing equipment and insect breeding equipment used for farming of subsequent stages of the insect life cycle are better used with regard to their run time, preferably optimally used for insect farming during a prolonged period of run time, according to the invention. Thus, according to the invention, the life insect transport device of the invention provides the opportunity to optimize or improve the efficiency of sequentially using rearing and breeding equipment for farming insects, with less or minimal down time, i.e. idle time, for each specific farming equipment which would be due to for example non-availability of a following colony at the right stage in the insect life cycle at the moment the equipment for farming such colony in such stage becomes idle.

Current practice of small scale insect farming encompasses placement of an ovisite comprising insect eggs with an age difference of for example 2-3 days, for two-three days above a tray comprising feed for the hatched neonate larvae, which fall on top of the feed once hatched. It is clear that this approach comes with the drawback, now solved by application of the live insects transport device of the invention, as here above outlined, that neonate larvae have an age difference of as large as 2-3 days, compared to the minutes to hours age difference now obtainable with the transport device of the invention, while still being able to provide the same numbers of larvae per batch.

In one embodiment, the live insects transport device according to the invention is a device wherein the coupler imbricatedly coupling the at least two fluid guiding members is provided with a further fluid discharge member comprising a connector configured to connect each further fluid discharge member to a source of fluid, and wherein the further fluid discharge member(s) is/are configured to reinforce from below the first laminar flow of fluid over the top surface of the at least one fluid guiding member from the distal end to the proximal end of the fluid guiding unit during operation of the transport device. This way, performance of the live insect transport device of the invention is further increased, since the further fluid discharge members are positioned such that fluid exiting the fluid discharge members at an adjusted and regulated speed and pressure adds to the laminar flow of fluid passing over the imbricatedly coupled fluid guiding members. The pressure at which the further fluid provided by the further fluid discharge members is released into the laminar flow of fluid is fine-tuned and adjusted in relation to the length of the flow path of the laminar flow of fluid between from the first fluid discharge member to the subsequent further fluid discharge member. It is appreciated that the longer the path between two subsequent flow discharge members, the higher the pressure at which the further fluid is provided through the further fluid discharge member(s), according to the invention. An advantage of providing the live insect transport device with the at least one further fluid discharge member, is that the laminar flow of fluid is more constant with regard to the velocity of the volume elements of fluid in the laminar flow, and is more constant with regard to the direction of the laminar flow of fluid from the distal end of the fluid guiding unit to the proximal end of the fluid guiding unit, according to the invention. Providing further fluid discharge member(s) at the indicated location in the transport device of the invention for example contributes to preventing live insects which are taken up by the laminar flow of fluid from bumping to the top surface of the fluid guiding units, or even sticking to said top surface, due to gravitation force. Providing further sources of fluid along the flow path of the laminar flow of fluid at least partly eliminates the effect of gravity on the live insects taken up by the fluid in the laminar flow. Thus, losses due to live insects released from the laminar flow of fluid along the path from the distal end of the fluid guiding member to the proximal end of said fluid guiding member is at least reduced, if not prevented according to the invention.

Furthermore, by application of further fluid discharge members along the path of the laminar flow of fluid, for reinforcing said laminar flow of fluid, a lower flow, that is to say a flow at lower pressure and/or at lower fluid velocity, is sufficient along the full length of the flow path in the live insect transport device, when compared to applying a single fluid discharge member at the distal end of the fluid guiding member. Applying such a lower flow by the application of multiple fluid discharge members avoids the occurrence of turbulence in the air surrounding the laminar flow of fluid at least to some extent. Turbulence increases with increasing fluid velocity and/or increasing air pressure, thus applying lower velocity and/or lower air pressure is beneficial to the efficiency of transporting live insects such as neonate larvae in the laminar flow of fluid, preventing the insects from being transferred to undesired directions due to turbulence. Applying the additional fluid discharge members at the locations of imbricated consecutive fluid guiding members thus provides a way to boost the laminar flow of fluid, such that the air pressure and/or air velocity is reduced, which provides better controllable transport of the neonate larvae in the laminar flow of fluid, e.g. air.

In one embodiment, the live insects transport device according to the invention is a device further comprising a casing covering the fluid guiding unit and the feeder arrangement.

In one embodiment, the live insects transport device according to the invention is a device further comprising a temperature control unit for controlling the temperature at the inner side of the casing and/or further comprising a unit for controlling relative air humidity at the inner side of the casing.

The live insects transport device of the invention provided with a casing provides for several further benefits with regard to efficiency of providing numbers of live insects within a certain time frame and having a certain minimal difference in age, according to the invention. The casing encloses for example the feeder arrangement and fluid guiding member in a manner that effectively a closed inner space is provided having openings for receiving the first and optionally further fluid discharge members and an opening at the proximal end of the fluid guiding member providing an exit for transported live insects, according to the invention. In such a closed inner space, temperature is controllable, such as automatically controllable at a selected temperature or selected temperature range. This way, reservoirs comprising live insects such as eggs, for example of black soldier fly, are maintainable at a controlled and predetermined temperature for stimulating optimal hatching. The same holds true for controllability of relative air humidity inside the cased live insect transport device, according to the invention. Typically, for optimal release of live insects from the reservoirs into the live insect receiving portion of the transport device of the invention, the temperature inside the cased live insect transport device of the invention is for example between 21° C. and 27° C., preferably about 26° C., when for example ovisites comprising eggs of black soldier fly are applied in the feeder arrangement, when the transport device is operating, according to the invention. Typically, for optimal release of live insects from the reservoirs into the live insect receiving portion of the transport device of the invention, the relative air humidity inside the cased live insect transport device of the invention is for example between 45% and 95%, preferably about 60% to 85%, when for example ovisites comprising eggs of black soldier fly are applied in the feeder arrangement, when the transport device is operating, according to the invention.

In one embodiment, the live insects transport device according to the invention is a device wherein the fluid is a gas. It is preferred that the fluid is a gas selected from gases such as air, ambient air, conditioned air with regard to temperature and/or relative humidity and/or enrichment of one or more gases with regard to the naturally occurring ratio and/or depletion such as partial depletion of one or more gases such as ammonia, methane, nitric oxides, with regard to the naturally occurring ratio and content, and/or addition of other gases than the naturally occurring gases of air, a mixture of oxygen and nitrogen, optionally the gas is humidified and/or temperature controlled air. Since insects commonly thrive well in ambient air, the application of ambient air, or just air, used in the first laminar flow is preferred, according to the invention. Of course, application of a liquid such as water, e.g. tap water or water comprising nutrients, is suitable as well, for the laminar flow of fluid in the live insect transport device of the invention, although a gas is preferred according to the invention. Live insects have a higher survival time in a gas such as ambient air, when compared to when the fluid is for example water. Furthermore, temperature control of a fluid which is a gas such as ambient air is less energy consuming than temperature control of a same volume of a liquid such as water in the laminar flow of fluid. Further benefits of applying a gas such as air for the laminar flow of fluid in the live insect transport device of the invention, over applying a liquid such as water, is that applying a liquid to transport live insects implies the necessity to use filters once the live insects such as neonate larvae, e.g. of black soldier fly, exited the transport device. The requirement to use filters results in increased steps in processing live insects, coming with an increased demand on time, labour and financial resources, and with an increased risk for system failures such as by clogging of filters, to name a few drawbacks relating to the application of a liquid, not apparent when using a gas such as air in the laminar flow of fluid, according to the invention.

In one embodiment, the live insects transport device according to the invention is a device wherein the gas is air. Furthermore, from a cost perspective, use of air as the fluid in the laminar flow of fluid is beneficial, especially for the insect farming at industrial scale, according to the invention. Preferably, according to the invention, the fluid in the laminar flow when the live insect transport device is in operation is temperature controlled air. Relative air humidity controlled air is also preferred. Taking up live insects released from reservoirs above the live insect receiving zone of the live insect transport device of the invention in the laminar flow of fluid wherein the fluid is air, preferably temperature controlled air and/or relative air humidity controlled air provides a measure to further contribute to maintaining the transported live insects in good health, and uninjured, according to the invention, since temperature and relative humidity of the gas surrounding the live insects once being transported in the laminar flow of fluid, are optimizable to the parameter values most suitable for preservation of health of the insects.

In one embodiment, the live insects transport device according to the invention is a device wherein the source of fluid comprises a compressor providing compressed fluid. Preferably, the compressed fluid is compressed gas, preferably compressed air, according to the invention. In one embodiment, the live insects transport device according to the invention, wherein the source of fluid comprises a pump, for driving fluid through the fluid discharge member. Preferably, the source of fluid comprises a pump such as a blower, for driving fluid through the fluid discharge member of the live insect transport device of the invention, wherein the fluid preferably is air, according to the invention.

A compressor and/or a pump provides the benefit of being able to controllable supplying the insect transport device of the invention with fluid at a pressure and at a volume of fluid per minute that contributes to the wellbeing of the live insects once taken up in the fluid of the laminar flow. That is to say, by selecting the optimal pressure and by selecting the optimal flow rate of fluid discharged from the first and optionally further fluid discharge members, for example a laminar flow of fluid is provided such that live insects obtain the same or similar velocity in meter per second as the fluid surrounding the insects once taken up in the laminar flow of fluid, according to the invention. Then, since fluid is not passing along the live insects in the laminar flow of fluid, unwanted effects of fluid flowing along insects is at least reduced and eliminated at best. For example, drying out of the live insects in the laminar flow of fluid is reduced or prevented, when the live insects move through the live insects transport device at the same or similar speed as the surrounding fluid. For example, cooling of live insects being transported by fluid passing insects is reduced or prevented as well by optimizing the pressure and fluid velocity with for example a pump or with a compressor such as an air compressor. In one embodiment, the live insects transport device according to the invention is a device wherein the fluid is temperature-controlled fluid and/or wherein the fluid is a relative humidity-controlled gas. Typically, the compressor or pump provides a fluid such as air which is discharged by the first and optionally further fluid discharge member(s) at a speed of between 1 m/sec and 100 m/sec, such as between 5 m/sec and 40 m/sec, preferably about 10-30 m/sec such as about 25 m/sec, according to the invention, such that a laminar flow of fluid is provided in the live insects transport device of the invention, having fluid flowing at the same or similar velocity. Typically, the compressor or pump provides an amount of fluid such as air at a volume of 10 $m^3$/hour to 320 $m^3$/hour, preferably about 20 $m^3$/hour to 60 $m^3$/hour, driven through the first and further fluid discharge members such that a laminar flow of fluid is provided having the same or similar flow rate of 1 $m^3$/hour to 30 $m^3$/hour, preferably about 5 $m^3$/hour to 15 $m^3$/hour, according to the invention. In one embodiment, the live insect transport device of the invention comprises a compressor or pump configured to provide an amount of fluid such as air at a volume of 2.5 $m^3$/hour to 1000 $m^3$/hour, preferably about 5 $m^3$/hour to 500 $m^3$/hour, more preferably of 10 $m^3$/hour to 320 $m^3$/hour, most preferably of about 20 $m^3$/hour to 60 $m^3$/hour, driven through the first and further fluid discharge members such that a laminar flow of fluid is provided having the same or similar flow rate of 0.2 $m^3$/hour to 70 $m^3$/hour, preferably about 0.5 $m^3$/hour to 50 $m^3$/hour, more preferably of 1 $m^3$/hour to 30 $m^3$/hour, most preferably of about 5 $m^3$/hour to 15 $m^3$/hour, according to the invention. These flow velocities and these flow rates are preferred since they contribute to optimally keeping the transported live insects in the live insects transport device of the invention in good condition, according to the invention.

In one embodiment, the live insects transport device according to the invention is a device wherein the feeder arrangement is configured to receive at least one reservoir for live insects at a predetermined distance above said live insects receiving portion of the top surface of the at least one fluid guiding member. Preferably, said predetermined distance between the at least one reservoir and the live insects receiving portion is between 3 cm and 35 cm, such as between 5 cm and 20 cm, preferably about 4 cm or about 6-9 cm, according to the invention.

Optimization of the distance between the reservoir and the insects receiving portion contributes to the efficiency of the process of taking insects up in the laminar flow of fluid in the live insects transport device of the invention. Optimization in this regard is providing the reservoir at a height above the laminar flow of fluid such that most if not all of the live insects released from the reservoir are taken up by the laminar flow of fluid, with minimal or no losses of live insects due to for example turbulent air streams, etc.

In one embodiment, the live insects transport device according to the invention is a device wherein at least the smooth top surface of the at least one fluid guiding member is made of any of stainless steel, aluminum, a polymer such as polypropylene and polyethylene, a polymer blend, or a combination thereof. A smooth top surface in the context of the invention refers to the top surface of the fluid guiding members being free of ridges, protrusions, recesses, etc., wherein the top surface is for example preferably polished or the like in order to provide for a surface which minimally hampers the laminar flow of fluid through the live insects transport device of the invention. The inventors found that a surface that is smooth does not prevent neonate larvae such as those from black soldier fly from sticking to such surface. That is to say, blowing a stream of air along the polished and smooth surface of e.g. a metal such as aluminum or stainless steel, with e.g. neonate larvae on top of said smooth surface, was not efficient and efficacious in transporting said larvae along the surface, according to tests performed by the inventors. Therefore, the inventors found that it is beneficial to keep the live insects airborne in the laminar flow of fluid in the live insect transport device of the invention. Thus, a polished and smooth top surface of the fluid guiding unit aids the unhampered laminar flow of e.g. air, and further contributes to the ease of cleaning the transport device of the invention.

In one embodiment, the live insects transport device according to the invention is a device wherein the tilt angle $\alpha$ is between 0° and 45°. Preferably, the tilt angle $\alpha$ is between 10° and 30°. Tilting the live insects transport device of the invention is in support of controlling the numbers of transported live insects exiting the transport device of the invention. For example, operating a high speed camera at the proximal end of the fluid guiding unit for, for example, counting the number of exiting transported live insects, is aided by providing a tilted transport device of the invention at an angle as indicated, such as 15° to 25° or about 20°. Tilting the transport device of the invention this way provides for the possibility to position a camera above the exiting live insects while also being able to position a lamp required for proper operation of the camera below the location where live insects exit the transport device of the invention, with a reduced risk or even without the risk for exiting transported live insects contaminating the lamp surface, according to the invention.

In one embodiment, the live insects transport device according to the invention is a device further comprising a live insect discharge member comprising a flat surface with a first end and a second end, the discharge member coupled with its first end to the proximal end of the fluid guiding unit. Providing the live insect transport device of the invention with such live insect discharge member has the benefit of providing the possibility to improve on directing the transported live insects while exiting the transport device. For example, such a live insect discharge member is a funnel ending at the proximal end with a smaller cross section than the cross section of the opening of the live insect transport device of the invention at the location of the proximal end of the fluid guiding member, according to the invention.

In one embodiment, the live insects transport device according to the invention is said live insects transport device further comprising a live insects counting device for counting live insects in the first laminar flow exiting the live insect transport device at the proximal end of the live insect discharge unit. Preferably the counting device is an electronic device such as a camera for counting live insects in the first laminar flow exiting the live insect transport device at the proximal end of the live insect discharge unit.

In one embodiment, the live insects transport device according to the invention is the live insects transport device wherein the counting device is a high-speed camera. Preferred is a high-speed camera such as a 9 kHz camera although various other high speed cameras having an imaging speed of between 2 kHz and 25 kHz are equally applicable. One of the many advantages of the live insect transport device of the invention is the provision of a relatively narrow stream of fluid comprising the transported live insects such as neonate larvae exiting the transport device via a funnel-shaped live insects discharge member, such that for example the live insects can be imaged and monitored in a relatively small surface area comprising a relatively high number of live insects per unit volume or unit area. For example, now a camera with a relatively smaller width is still applicable for imaging purposes, compared to a camera with a broader width, required to image live insects passing the camera while exiting the live insects transport device of the invention in a relatively broad and non-funneled laminar flow of fluid. Cost saving is then one of the advantages of the invention.

In one embodiment, the live insects transport device according to the invention is a device wherein the reservoir for live insects is an insect egg collection interface or an insect egg holder, i.e. an ovisite. According to the invention, a live insects transport device comprises as the reservoir for live insects an ovisite such as a honey comb.

In one embodiment, the live insects transport device according to the invention is a device wherein the feeder arrangement is configured to receive between 2 and 250 reservoirs, preferably between 10 and 100, more preferably about 32 or about 64 reservoirs for releasing live insects above the live insects receiving portion.

In one embodiment, the live insects transport device according to the invention is arranged to transport any one or more of insect larvae, insect eggs, insect prepupae and insect pupae. Preferably, the live insects transport device according to the invention is arranged to transport any one or more of insect larvae, insect eggs, insect prepupae and insect pupae, wherein the insect larvae, insect eggs, insect prepupae and insect pupae are live insect larvae, live insect eggs, live insect prepupae and live insect pupae. Preferably the live insects transported by the live insects transport device of the invention are live insect larvae of black soldier fly, more preferably live neonate larvae of black soldier fly, according to the invention. In one embodiment, the live insects transport device according to the invention is arranged to transport live insects.

In one embodiment, the live insects transport device according to the invention is arranged to transport live neonate insect larvae.

In one embodiment, the live insects transport device according to the invention is arranged to transport live black soldier flies.

In one embodiment, the live insects transport device according to the invention is a device wherein the feeder arrangement is configured to receive the at least one reservoir in a predetermined orientation relative to the direction of the path for the first laminar flow of fluid, such that a major surface of the reservoir(s) is oriented perpendicular to the direction of said first laminar flow of fluid. Positioning reservoirs which have a major surface this way contributes to avoiding occurrence of any turbulence at the location of the reservoirs, at the location of the live insect receiving portion, therein between, and alongside the laminar flow of fluid. It will be appreciated that limiting any disturbing influence of turbulent air around live insects on their way from the reservoir to the live insects receiving portion, and while taken up and transported by the laminar flow of fluid, contributes to increasing the efficiency of the transport with regard to the numbers of successfully transported live insects by the live insect transport device of the invention, while in operation.

In one embodiment, the live insects transport device according to the invention is a device wherein the live insects receiving portion further comprises side walls located along longitudinal sides of the at least one longitudinal fluid guiding member, the side walls being tilted at an obtuse angle relative to the top surface of the at least one fluid guiding member,

- wherein each side wall having a top side and a bottom side, the bottom side being connected to a longitudinal side of the at least one longitudinal fluid guiding member, and a smooth surface arranged between the bottom side and the top side, and
- wherein the top side of each side wall is provided with at least a second fluid discharge member, each second fluid discharge member being located at the top side of each side wall and comprising a connector configured to connect the second fluid discharge member to a source of fluid, for providing a second laminar flow of fluid over the surface of the side walls from the top side of the side walls to the path of the first laminar flow of fluid during operation of the transport device, and wherein the second laminar flow of fluid is oriented perpendicular to the first laminar flow of fluid.

Providing the live insects transport device of the invention with a live insects receiving portion further comprising the indicated side walls contributes to improved capacity of the transport device of the invention when the duration of operation at constant supply of a certain number of transported live insects exiting the transport device is taken into account, and/or when the numbers of live insects exiting the transport device per time unit is taken into account. With such side walls tilted at an obtuse angle relative to the top surface of the at least one fluid guiding member, the capacity of the feeder arrangement is enlarged while the laminar flow of fluid is kept at the same size and volume and flow rate, according to the invention. The second laminar flow of fluid, preferably air, is directed perpendicular to the direction of the first laminar flow of fluid, and the flow rate and/or the pressure at which the fluid exits the second fluid discharge member for building up the second laminar flow of fluid, is/are lower than those for the first laminar flow of fluid running from the distal end of the fluid guiding member to the proximal end thereof, according to the invention. These differences in flow rate and/or fluid pressure contribute to the reduction or even to the avoidance of undesired turbulence anywhere in the proximity of live insects, such as inside the cases live insects transport device of the invention.

A second aspect of the current invention relates to a method for transporting live neonate insect larvae comprising the steps of:
providing an ovisite comprising insect eggs;
providing a live insect transport device;
providing a laminar flow of air in the transport device;
placing said ovisite in a feeder arrangement of said transport device; and
transport live neonate insect larvae upon hatching of said larvae in the ovisite by taking up the neonate insect larvae in the first laminar flow of air.

A third aspect of the current invention relates to the use of the live insect transport device of the invention for dosing live neonate insect larvae, wherein live neonate insect larvae transported by said transport device are collected at the proximal end of the fluid guiding unit comprised by the transport device or at the second end of the insect discharge member comprised by the transport device, in a first receptacle for a period of time until a predetermined number of live neonate insect larvae passed said proximal end of the fluid guiding unit or said second end of the insect discharge member, such that a dose of live neonate insect larvae is provided.

In one embodiment, use of the live insect transport device according to of the invention, is the use of the device wherein the predetermined number of live neonate insect larvae is established by a counting device for counting live insects in the first laminar flow exiting the live insect transport device.

In one embodiment, the method according to the invention or the use according to the invention, are applied with black soldier flies.

In one embodiment, the method according to the invention or the use according to the invention are applied with air in the first laminar flow which is temperature controlled air at a temperature of between 22° C. and 30° C. Preferred is a temperature of about 25° C. to 28° C.

In one embodiment, the method according to the invention or the use according to the invention, are applied with the air in the first laminar flow being relative-humidity controlled air with a relative humidity of between 40% and 90%, such as about 60% to 75%.

In one embodiment, the method according to the invention or the use according to the invention are applied with the air in the first laminar flow having a speed of between 10 m/sec and 70 m/sec.

In one embodiment, the method according to the invention or the use according to the invention are applied with the air in the first laminar flow having a pressure at the location of the fluid discharge member of between 10 bar and 0.8 bar.

In yet a fourth aspect, the present invention relates to a combination of a cyclone separation system and one or more live insect larvae transport devices connected to the cyclone separation system, wherein the cyclone separation system comprises a main cyclone chamber having a top chamber part and a conical shaped bottom chamber part, wherein the top chamber part is connected to one or more intake channels each of which is arranged for connection to a live insect larvae transport device of the one or more live insect larvae transport devices, and wherein the bottom chamber part is connected to a discharge nozzle comprising a discharge end having a main discharge conduit for discharging live insects from the cyclone separation system, and wherein the discharge end comprises an air injection member for connection to a secondary air source and wherein the air injection member is configured to inject air back into the discharge nozzle.

Definitions

The term "live" has its regular scientific meaning and here refers to an organism that is in a healthy condition and that has a normal average life expectation.

The term "transport" has its regular scientific meaning and here refers to taking an item, here in the context of the invention an insect such as live neonate insect larvae, from a first location to a second location with the help of a transportation means, here a fluid such as a gas.

The term "air" has its regular scientific meaning and here refers to the air surrounding the earth at ground level.

The term "ambient" has its regular scientific meaning and here refers to that what is surrounding something. Ambient air thus refers to the air surrounding the live insects transport device, according to the invention.

The term "insect" has its regular scientific meaning and here refers to all stages of an insect, e.g. pupae, adult insect, neonate larvae, larvae, prepupae.

The term "high-speed" has its regular scientific meaning and here refers to a speed of acquiring images of at least 30 per second to 20.000 per second such as about 15.000 images per second. For example high-speed imaging is imaging with exposures of less than 1/1.000 second or frame rates in excess of 250 frames per second in the context of the invention.

The term "longitudinal" has its regular scientific meaning and here refers to the direction running from the distal end of the fluid guiding units and the distal fluid guiding members in the direction of the proximal end of the fluid guiding units and the proximal fluid guiding members, of the live insect transport device of the invention.

The term "imbricatedly" or "imbricated" has its regular scientific meaning and here refers to the arrangement of essentially planar bodies such that they stack in a consistent fashion.

The term "casing" has its regular scientific meaning and here refers to an enclosure enclosing here (most of) the parts and components of the live insects transport device of the invention.

The term "reservoir" has its regular scientific meaning and here refers to a receptacle, e.g. a container, a tray, a funnel, a sieve, a cup, etc., such as an ovisite, with at least an open side for allowing live insects exiting the reservoir and subsequently moving in the direction of the live insect receiving portion between the distal end and proximal end of the at least one fluid guiding member of the live insect transport device of the invention.

BRIEF DESCRIPTION OF THE DRAWINGS

FIG. 1 displays an overview of an embodiment of the invention, showing a live insects transport device 1. The live insects transport device is tilted relative to the horizontal over an angle α. Further, an insect discharge member 11 is indicated, provided with a camera 8 and a lamp 9.

FIG. 2 displays an overview of a live insects transport device 1 of the invention comprising a casing 5 and a fluid guiding unit 12 that provides a smooth longitudinal path for a laminar flow of fluid, and further displays the distal end 15 of the fluid guiding unit which receives the fluid discharge members 20, 20' through an opening 17 in the casing 5.

FIG. 3 displays a detailed side view of a live insects transport device 1 of the invention where the proximal end of the fluid guiding unit 12' ends and where the insect discharge member (See also 11 in FIG. 2) is located and coupled to said proximal end.

FIG. 4 displays an inside view of a live insects transport device of the invention. Shown are longitudinal fluid transport members 12', 12" which are connected imbricatedly at positions 21, 22 and 21', 22'. Where two consecutive fluid transport members are coupled imbricatedly, a fluid discharge member (See 20, 20' in FIGS. 2 and 114', 114", 114'" in FIG. 5) is positioned at the location where said fluid transport members overlap, said fluid discharge member provided with openings 23, 23' for discharging fluid.

FIG. 5 displays an overview of another embodiment of the invention, showing a live insects transport device 100 comprising a live insects receiving portion that is built up by a fluid guiding unit 112 comprising side walls 113 tilted at an obtuse angle relative to the top surface of the fluid guiding members. The live insects transport device of the embodiment comprises a casing 105, said casing having a top side 102 made at least in part from a transparent material 125 such as a plate made of glass.

FIG. 6 displays a part of a live insects receiving portion of a live insects transport device 100 of the invention, the live insects receiving portion being built up by a fluid guiding unit 112' comprising side walls 113' and 113" tilted at an obtuse angle relative to the top surface of the fluid guiding members. Further displayed are the proximal end 121" of the live insects guiding unit 112' and the further fluid discharge members 131 and 131' located at the top side of the side walls, and the feeder arrangement 127 located above the live insects receiving portion of the top surface of the fluid guiding unit.

FIG. 7 displays a view of a live insects transport device 100 of the invention along the longitudinal fluid guiding units in the direction towards the first fluid discharge member located at opening 117. Consecutive fluid guiding units are connected imbricatedly and at positions where the fluid guiding units overlap imbricatedly further fluid discharge members are located for reinforcing the first laminar flow of fluid. The live insects receiving portion is shown and is built up by a fluid guiding unit 112' comprising side walls 113' and 113" tilted at an obtuse angle relative to the top surface of the fluid guiding members. Further displayed are the distal end of the live insects guiding unit and the further fluid discharge members 131' and 131 located at the top side of the side walls 113" and 131', respectively.

FIG. 8 depicts a live insect larvae transport device 100 comprising a fluid guiding unit 112 and arched convex side walls 113', 113" arranged there along according to an embodiment of the present invention;

FIG. 9 depicts a live insect larvae transport device 100 comprising a cover member 132 arranged over and along a fluid guiding unit 112 according to an embodiment of the present invention;

Figure 12:
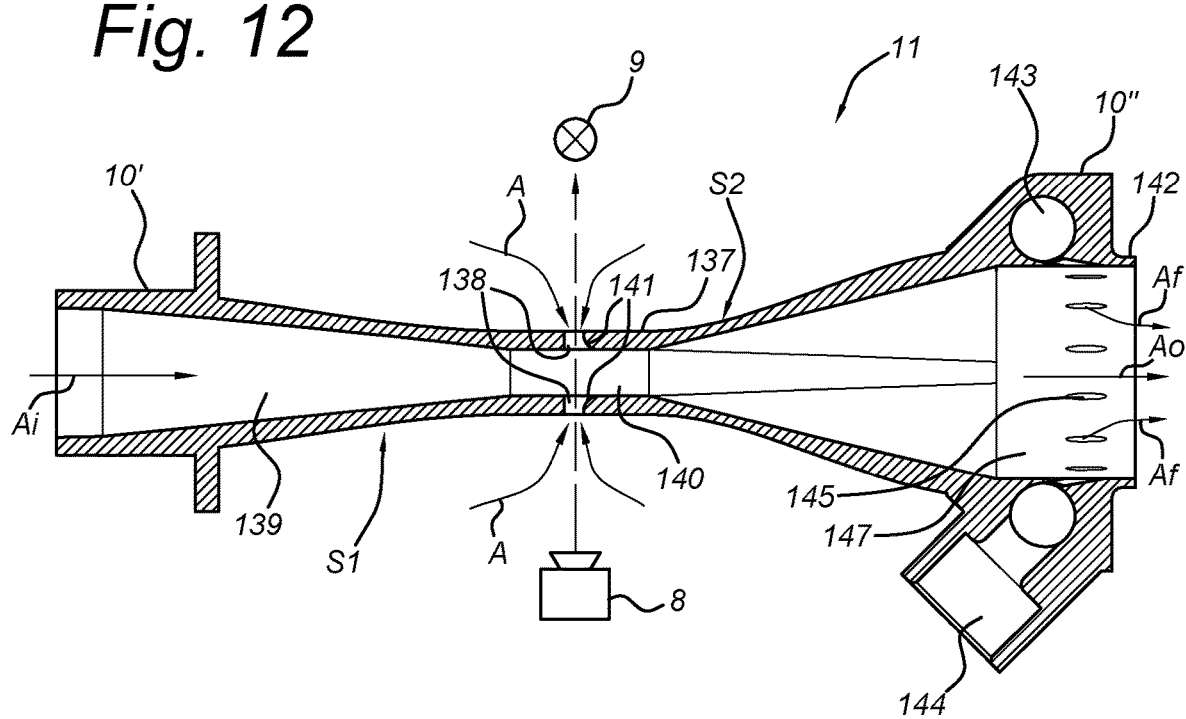
Figure 13:
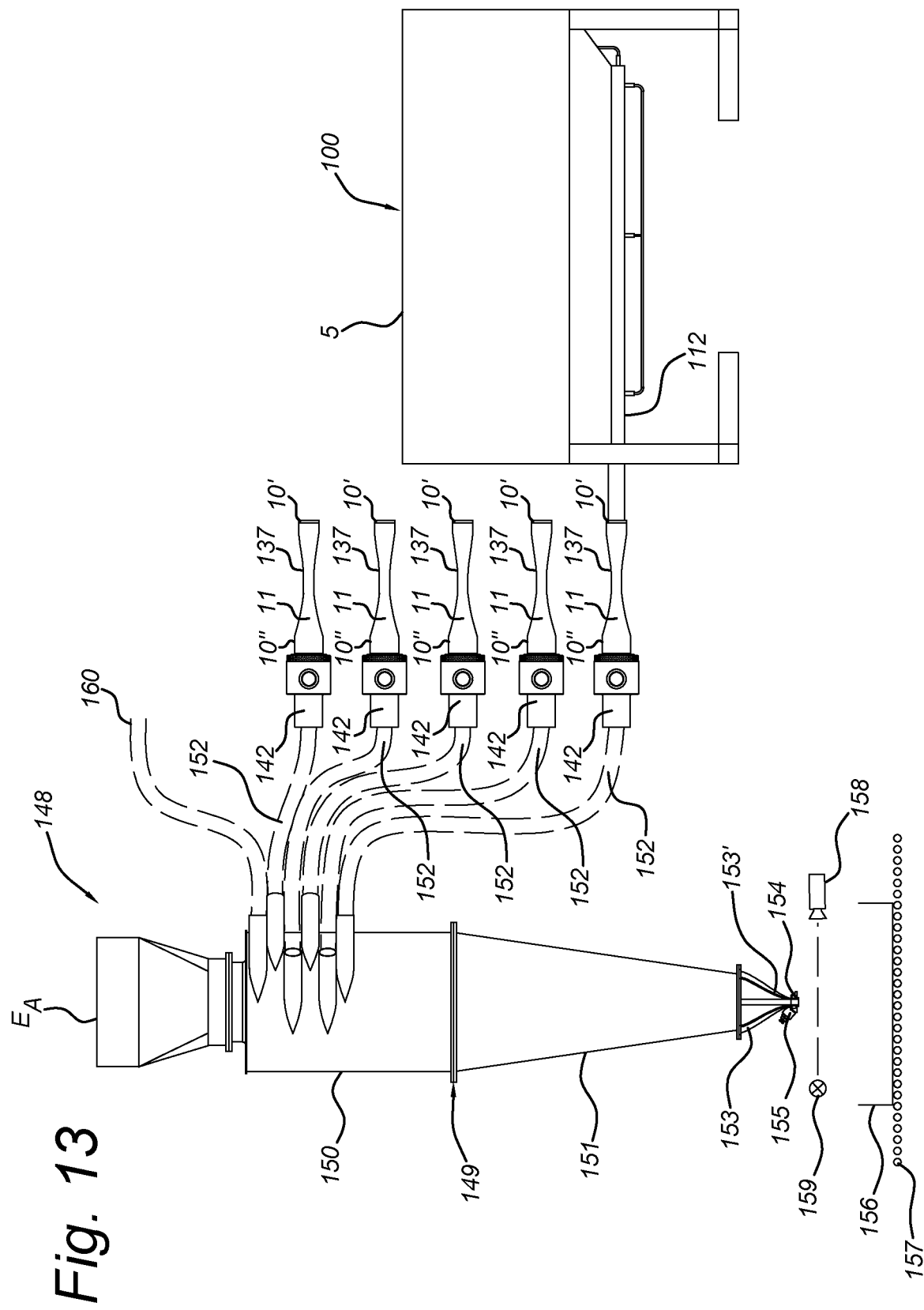

FIG. 12 shows a cross sectional view of a live insect discharge member 11 according to an embodiment of the present invention; and wherein FIG. 13 shows a schematic view of a combination of a cyclone separation system 148 and one or more live insect larvae transport devices 100 according to an embodiment of the present invention.

DETAILED DESCRIPTION OF EMBODIMENTS

Referring to FIG. 1, an overview of an embodiment of the invention is provided, showing a live insects transport device 1. The live insects transport device is tilted relative to the horizontal over an angle α. Further, an insect discharge member 11 is indicated, provided with a camera 8 and a lamp 9 at the proximal end 10 of the live insect discharge member 11, which is coupled at its distal end 10' to the opening in the side wall 7 of casing 5, at the proximal end 26 of the live insect transport device 1. The camera 8 is a high-speed imager able to detect, image and store images at the speed required for counting and dosing larvae exiting the live insect transport device through the opening of the live insect discharge member located at proximal end 10. Other measurements like determination of lipid content by application of near infra red spectroscopy, could also be performed, for example. The live insects transport device is coupled to a frame 16, amongst others for the purpose of tilting the transport device over said angle α. Positioning the transport device 1 over said angle prevents larvae from contaminating the lamp 9, positioned in the proximity of the opening of the live insect discharge member 11. The live insects transport device comprises a fluid guiding unit 12 comprising upright side walls 13. The transport device further comprises a casing 5 covering the fluid guiding unit and the feeder arrangement (not shown), the casing comprising a top wall 2, side walls 3, 4, 7. At the distal end 6 of the live insects transport device 1, the distal end 15 of the fluid guiding unit 12 is located. Here, a first fluid discharge member (not shown) is located, being configured to connect to a source of fluid 200. The source of fluid comprises a pump or a compressor 14', and the fluid is provided to the live insects transport device via tubing or pipes 14, connecting the source of fluid to fluid discharge members.

Now referring to FIG. 2, a drawing is displayed providing an overview of a live insects transport device 1 of the invention comprising a casing 5 and a fluid guiding unit 12 that provides a smooth longitudinal path for a laminar flow of fluid, and further displays the distal end 15 of the fluid guiding unit which receives the fluid discharge members 20, 20' through an opening 17 in the casing 5. The fluid discharge members 20, 20' are coupled to a source of fluid (not shown) with tubing 19 and 19', said tubing coupled to the fluid discharge members with couplers 18, 18'. The live insects transport device is further provided with a live insects discharge member 11.

Figure 3:
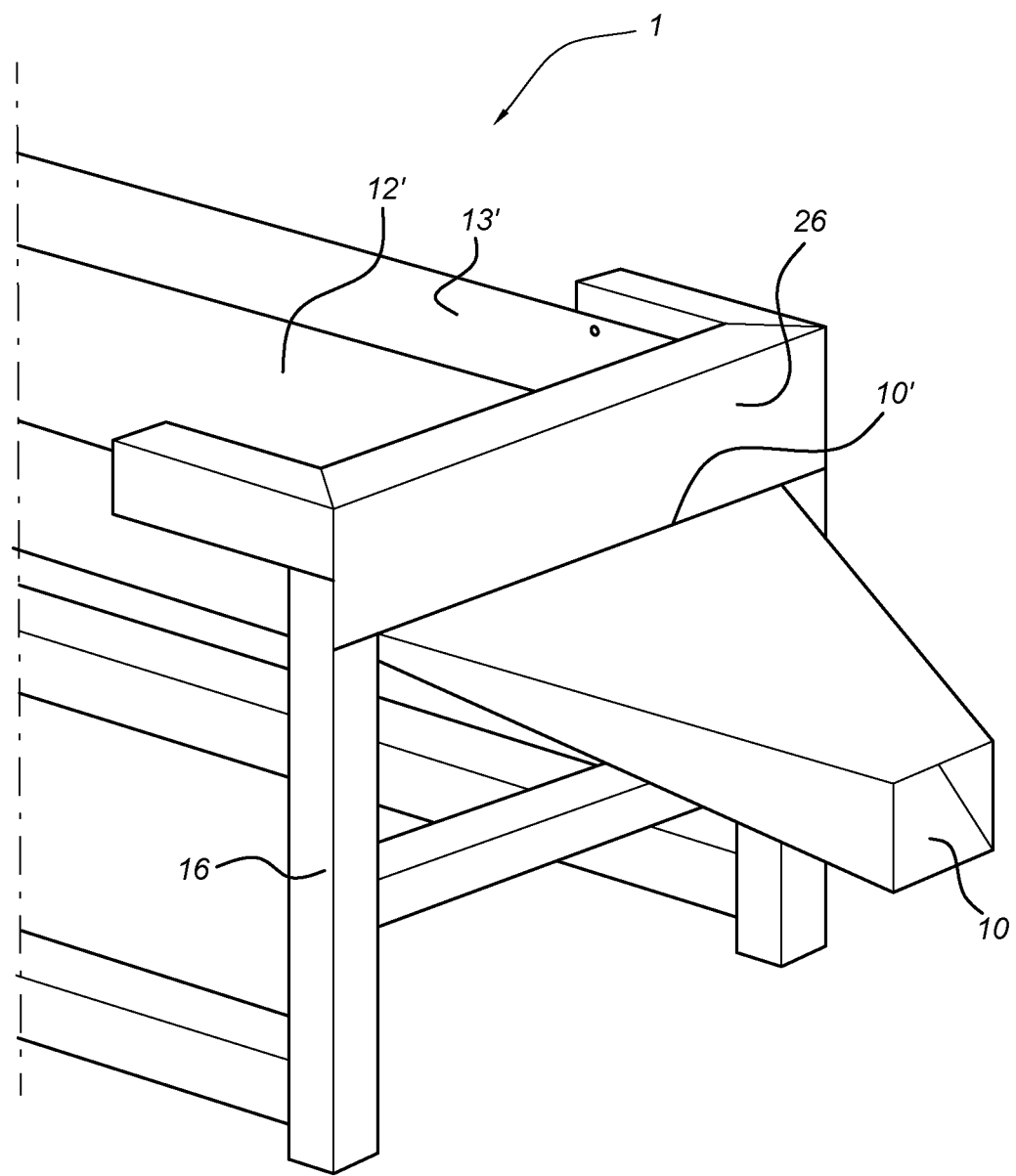

Now referring to FIG. 3, a drawing is displayed providing a detailed side view of a live insects transport device 1 of the invention where the proximal end 26 of the fluid guiding unit 12' ends and where the insect discharge member (See also 11 in FIG. 2) is located and coupled to said proximal end with the distal end portion 10' of the live insects discharge member. The live insects discharge member has a funnel-like shape according to the invention, configured to provide a narrowed stream of flowing live insects in the flow of fluid exiting the live insects transport device. Narrowing the stream of live insects provides the benefit of a smaller cross section of the flow of fluid comprising the live insects, in support of counting, sorting and/or dosing the insects. The fluid guiding member comprises upright side walls 13'. The live insect receiving zone is provided by the smooth top surface of the fluid guiding member 12'.

Figure 4:
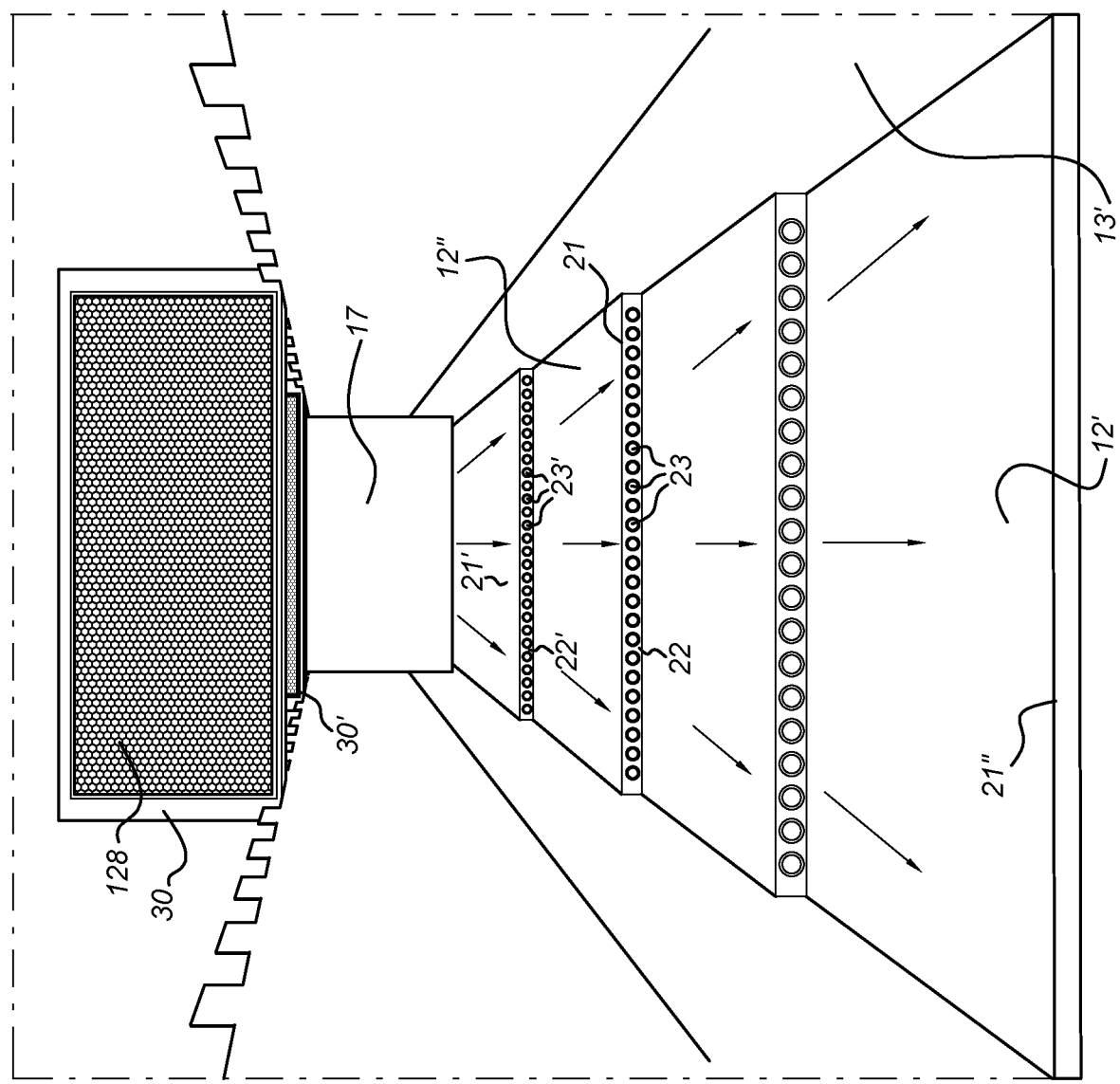

Now referring to FIG. 4, a drawing is displayed providing an inside view of a live insects transport device of the invention. Shown are longitudinal fluid transport members 12', 12" which are connected imbricatedly at positions 21, 22 and 21', 22'. Where two consecutive fluid transport members are coupled imbricatedly, a fluid discharge member (not shown; See 20, 20' in FIGS. 2 and 114', 114", 114''' in FIG. 5) is positioned at the location where said fluid transport members overlap, said fluid discharge member provided with openings 23, 23' for discharging fluid. In this embodiment, the live insects receiving portion is provided by the smooth top surface of four imbricatedly coupled fluid guiding units, two of which are indicated with 12' and 12". The transport device has straight upright walls 13'. The laminar flow of fluid is in the direction of the arrows, flowing to the proximal end 21" of the proximal fluid guiding member 12'. The feeder arrangement (see 127 in FIG. 6) here received a frame 30, 30', encompassing a reservoir 128 for releasing live insects above the live insects receiving portion provided by the smooth top surface of the fluid guiding unit.

Figure 5:
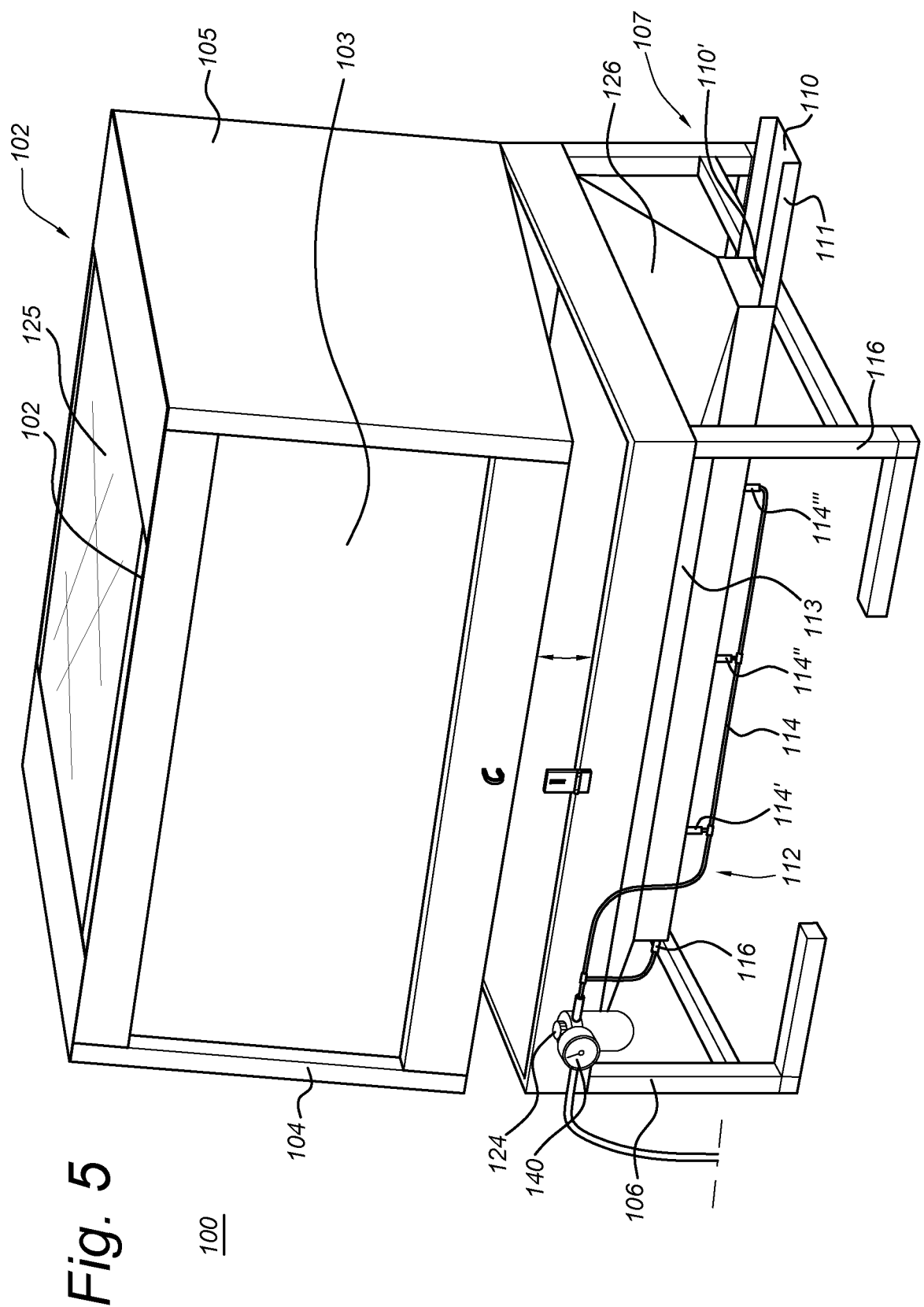

Now referring to FIG. 5, a drawing is displayed providing an overview of another embodiment, showing a live insects transport device 100 of the invention comprising a live insects receiving portion that is built up by a fluid guiding unit 112 comprising side walls 113 tilted at an obtuse angle relative to the top surface of the fluid guiding members. The live insects transport device of the embodiment comprises a casing 105, said casing comprising side walls 103, 104 and a top side 102, the top side made at least in part from a transparent material 125 such as a plate made of glass, a transparent polymer or polymer blend, etc. The live insects transport device 100 is provided with a live insects discharge member 111, coupled to the transport device at its distal end 110' at an opening 107 located at the proximal end 126 of the transport device, the live insects discharge member further comprising a proximal end where the laminar flow of fluid comprising live insects exits the discharge member. The live insect transport device is provided on a frame 106, 116. Fluid discharge members 114', 114" and 114''' are coupled to a fluid source via tubing 114, the fluid source comprising a compressor unit 124 comprising a pressure control unit 140. Fluid discharge members 114', 114" and 114''' are configured to provide a flow of fluid for reinforcing the laminar flow of fluid discharged into the live insects transport member at the distal end of the fluid guiding unit.

Figure 6:
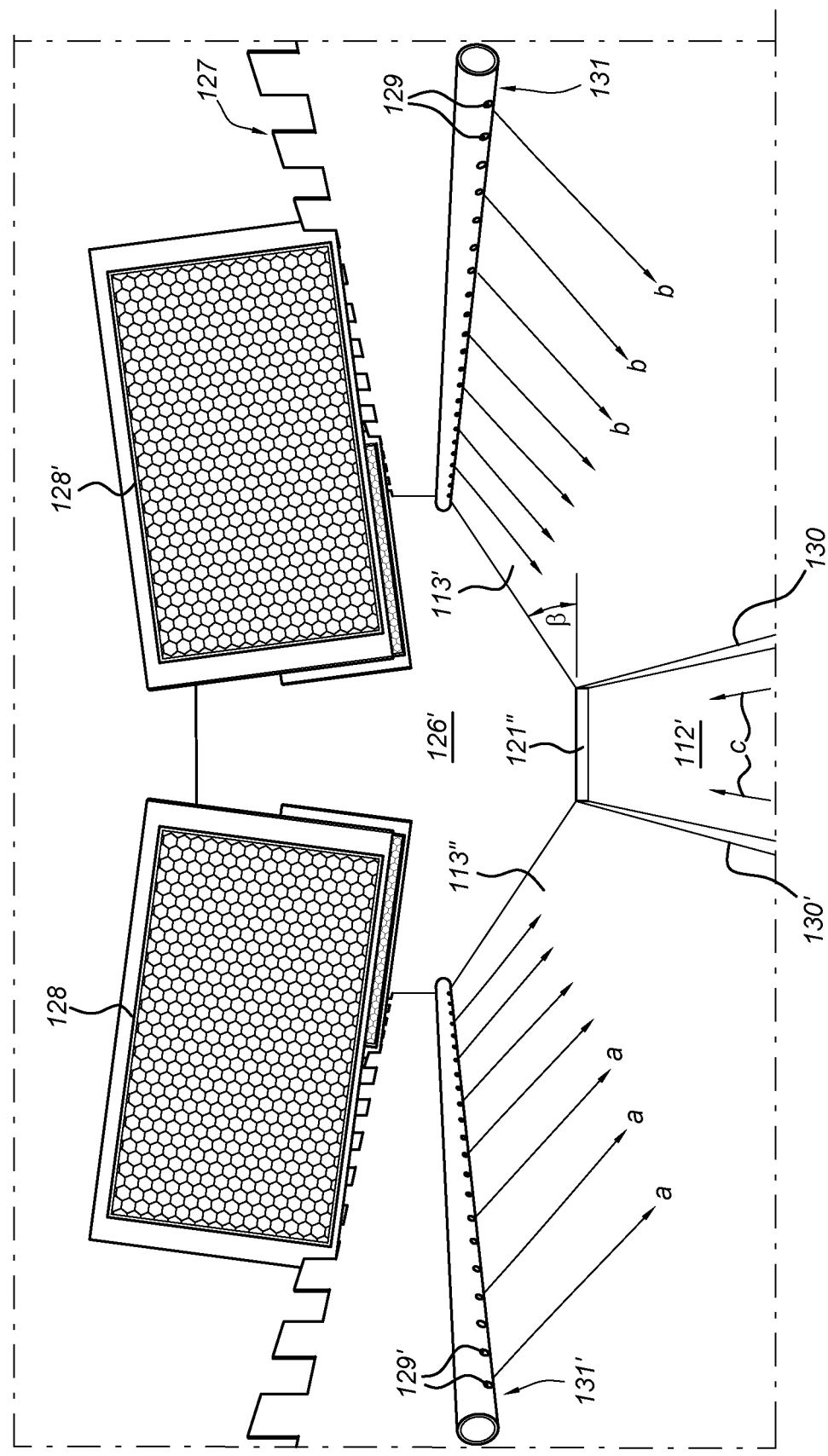

Now referring to FIG. 6, a drawing is displayed providing a view on part of a live insects receiving portion of a live insects transport device 100 of the invention, the live insects receiving portion being built up by a fluid guiding unit 112' comprising side walls 113' and 113" tilted at an obtuse angle (β) relative to the top surface of the fluid guiding members. Further displayed are the proximal end 121" of the live insects guiding unit 112' and the further fluid discharge members 131 and 131' located at the top side of the side walls, and the feeder arrangement 127 located above the live insects receiving portion of the top surface of the fluid guiding unit. A first laminar flow of fluid, such as a laminar flow of air, is provided in the direction of the arrows c towards the direction of the location of the proximal end 121" of the live insects guiding unit 112'. A further laminar flow of fluid, yet at a lower pressure and/or at a lower velocity in m³/sec, than the pressure and/or velocity of the fluid in the first laminar flow, is provided in the direction of the arrows a and b, provided by the fluid discharge members 131' and 131, respectively, wherein fluid is discharged through openings 129' and 129, respectively. The feeder arrangement 127 received frames, encompassing a reservoir 128, 128' for releasing live insects above the live insects receiving portion provided by the smooth top surface of the fluid guiding unit.

Figure 7:
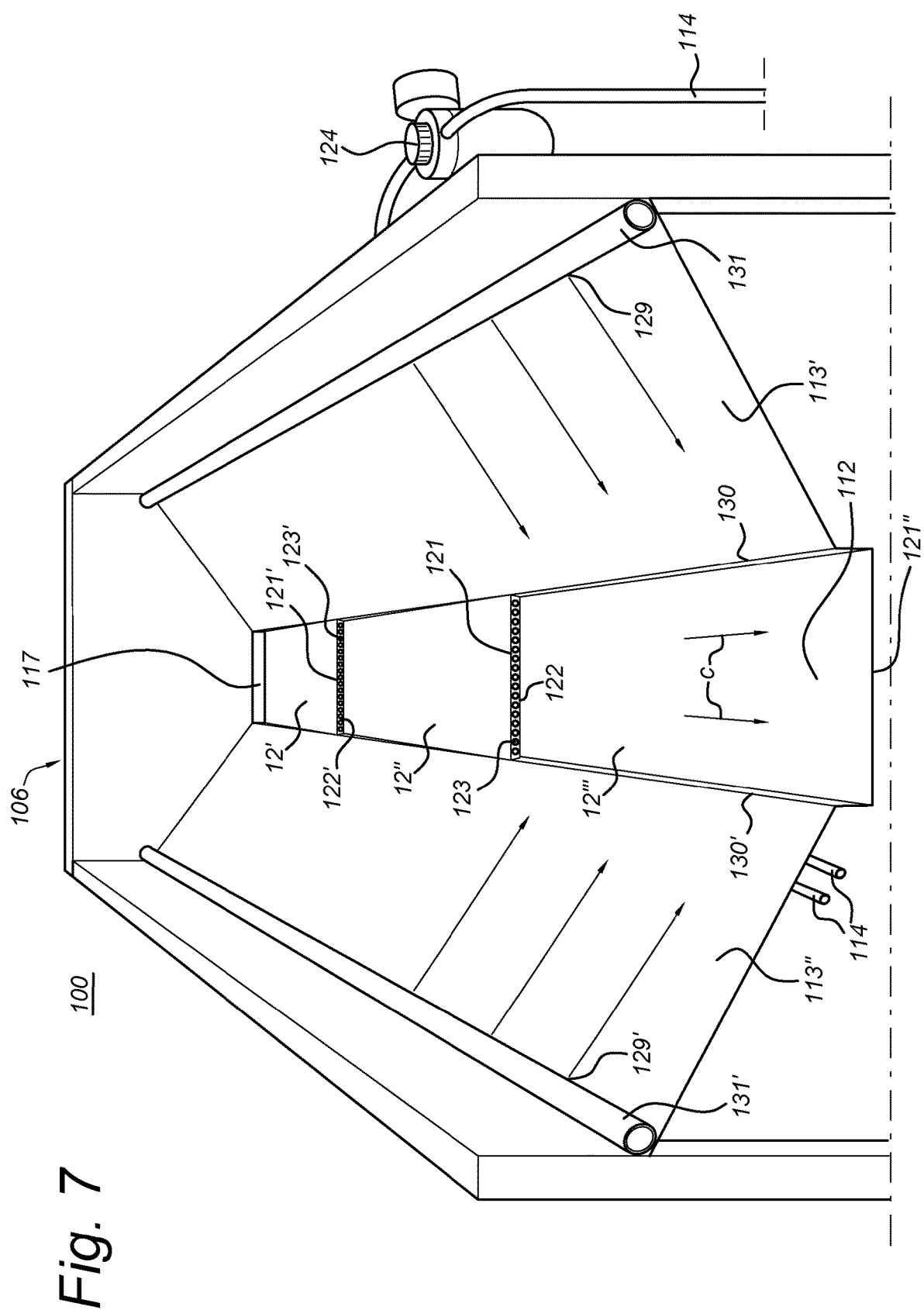

Now referring to FIG. 7, a drawing is displayed providing a view of a live insects transport device 100 of the invention along the longitudinal fluid guiding units in the direction towards the first fluid discharge member located at opening 117 in the side wall 106 of the transport device 100. Consecutive fluid guiding units are connected imbricatedly and at positions where the fluid guiding units overlap imbricatedly further fluid discharge members are located for reinforcing the first laminar flow of fluid. The live insects receiving portion is shown and is built up by a fluid guiding unit 112 comprising side walls 113' and 113", e.g. flat side walls 113', 113", tilted at an obtuse angle relative to the top surface of the fluid guiding members. Further displayed are the distal end of the live insects guiding unit and the further fluid discharge members 131' and 131 located at the top side of the side walls 113" and 131', respectively. The fluid discharge members located at positions where consecutive fluid guiding members imbricatedly overlap, i.e. positions 121', 122' (i.e. overlap between the proximal end 121' of a first fluid guiding member and the distal end 122' of a consecutive fluid guiding member) and 121, 122 (i.e. overlap between the proximal end 121 of the second fluid guiding member and the distal end 122 of a consecutive third fluid guiding member), are provided with openings 123', 123 for providing the first laminar flow of fluid in the direction of the arrows c. Further fluid discharge members 131' and 131 are provided with openings 129' and 129, for releasing fluid such that a laminar flow of fluid over the surface of tilted side walls 113" and 113' is provided in the direction of the arrows, perpendicular to the direction of the first laminar flow of fluid. Fluid discharge members are coupled to a source of fluid such as compressed air or a driver for driving air through the fluid discharge members such as a pump or a fan, via tubing or pipes 114, the source of fluid optionally comprising a control unit 124 for example for controlling the fluid pressure at entrance of the live insect transport device and/or for controlling the velocity of the fluid provided for the build up of the first and further laminar flows of fluid.

Figure 8:
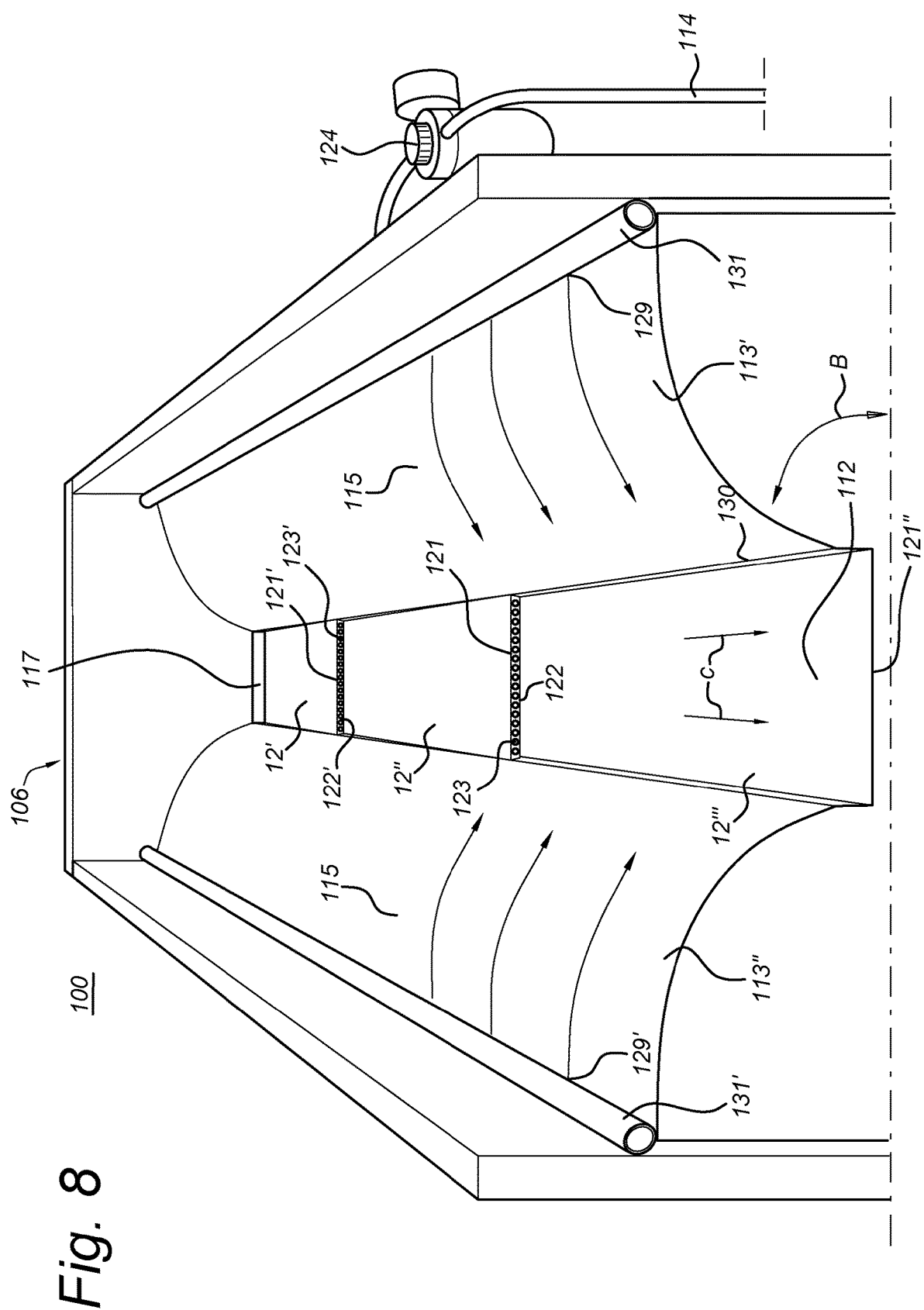

FIG. 8 shows an alternative embodiment of the embodiment shown in FIG. 7 of a live insect larvae transport device 100, wherein the live insects receiving portion further comprises convex side walls 113', 113", i.e. two opposing convex side walls 113', 113", located along longitudinal sides of the at least one longitudinal fluid guiding member 12', 12", 12''', e.g. three longitudinal fluid guiding members 12', 12", 12''', wherein each convex side wall 113', 113" has a top side and a bottom side, and a smooth convex surface 115 arranged and extending there between, and wherein the bottom side is connected to a longitudinal side of the at least one longitudinal fluid guiding member 12', 12", 12'''. As further depicted, the top side of each convex side wall 113', 113" is provided with a second fluid discharge member 131, 131' comprising a connector configured to connect the second fluid discharge member 131, 131' to a source of gas for providing a second laminar flow of gas over the surface 115 of the convex side wall 113', 113" from the top side thereof to the at least one fluid guiding member 12', 12", 12''' during operation of the live insect larvae transport device.

In contrast to the embodiment shown in FIG. 7, in the embodiment of FIG. 8 each side wall 113', 113" is a convex side wall 113, 113" having a top side provided with a second fluid discharge member 131, 131' comprising openings 129, 129' for discharging a gas, e.g. air, such that the second laminar flow of gas follows the convex surface 115 toward the at least one longitudinal fluid guiding member 12', 12", 12'''.

The convex side walls 113', 113" exhibit the advantageous effect in that when gas such as air flows over the convex side walls 113', 113" toward the top surface of the at least one fluid guiding member 12', 12", 12''', the speed of gas is maintained to a higher degree compared to gas flowing over flat side walls 113', 113" as shown in the embodiment of FIG. 7.

For example, when a gas such as air is discharged from the second fluid discharge members 131, 131' at a speed of 4 m/sec over flat side walls 113', 113" as depicted in FIG. 7, then the air may approach the top surface of the at least one fluid guiding member 12', 12", 12''' at a speed of about 2 m/s. On the other hand, for convex side walls 113', 113" as shown in FIG. 8, in order to reach 2 m/s air speed at the top surface of the at least one fluid guiding member 12', 12", 12''', then air may be discharged from the second fluid discharge members 131, 131' at a lower speed of e.g. 3 m/s.

In a further example, in case air is discharged from the second fluid discharge members 131, 131' at a speed of about 1.2 m/sec, then the air may approach the top surface of the fluid guiding members at a speed of about 0.4 m/sec, which is sufficient to maintain suspension of live insects in the first laminar flow of gas, e.g. air, over the top surface of the at least one fluid guiding member 12', 12", 12'''.

Therefore, gas flowing over the convex side walls 113', 113" maintains its speed to a much higher degree and a such less gas needs to be discharged by the second fluid discharge members 131, 131' for facilitating laminar flow over the top surface of the at least one fluid guiding member 12', 12", 12''' for transport of the live insects.

As the convex side walls 113', 113" allow for lower speeds of air being discharged from the second fluid discharge members 131, 131' with minimal loss of momentum, the discharged air has less impact on e.g. environmental conditions (e.g. temperature, humidity) surrounding the reservoirs comprising the live insects. For example, when a casing 5 is provided covering the fluid guiding unit 112 and the feeder arrangement as mentioned above, then the convex side walls 113', 113" allow air to be discharged toward the top surface of the at least one fluid guiding member 12', 12", 12''' with reduced impact on environmental conditions on the inner side of the casing 5.

It is further noted that when a gas such as air flows over the convex side walls 113', 113", then the gas tends to closely follow and "stick" to the convex side walls 113', 113" in substantially laminar fashion so that turbulence is kept to a minimum. As a result, laminar flow over the convex side walls 113', 113" reduces the amount of conditioned air being disturbed or pulled away from the at least one reservoir 128, 128' (see FIG. 6) and as such the laminar flow over the convex side walls 113', 113" reduces the amount of conditioned air being disturbed or pulled away from insect eggs contained in the at least one reservoir 128, 128'.

In an embodiment, the convex side walls 113', 113" engage the top surface of the at least one fluid guiding member 12', 12", 12''' at an angle (β) between 45 and 60°, such that (laminar) air flowing over the convex side walls 113', 113" causes minimum disturbance of conditioned air around insect eggs contained in the at least one reservoir 128, 128'.

For example, relative humidity of air at 1 bar around the insect eggs may be 80-85% at a temperature of 28° C. to 35° C.+/−0.5° C. The second fluid discharge members 131, 131' may then discharge a gas, e.g. air, at 1 bar at a temperature of 20° C. to 30° C. and with relative humidity of 40%-55%, e.g. 45%. As the discharged air flows in substantially laminar fashion over the convex side walls 113', 113" in a temperature controlled manner, condensation is prevented.

Figure 9:
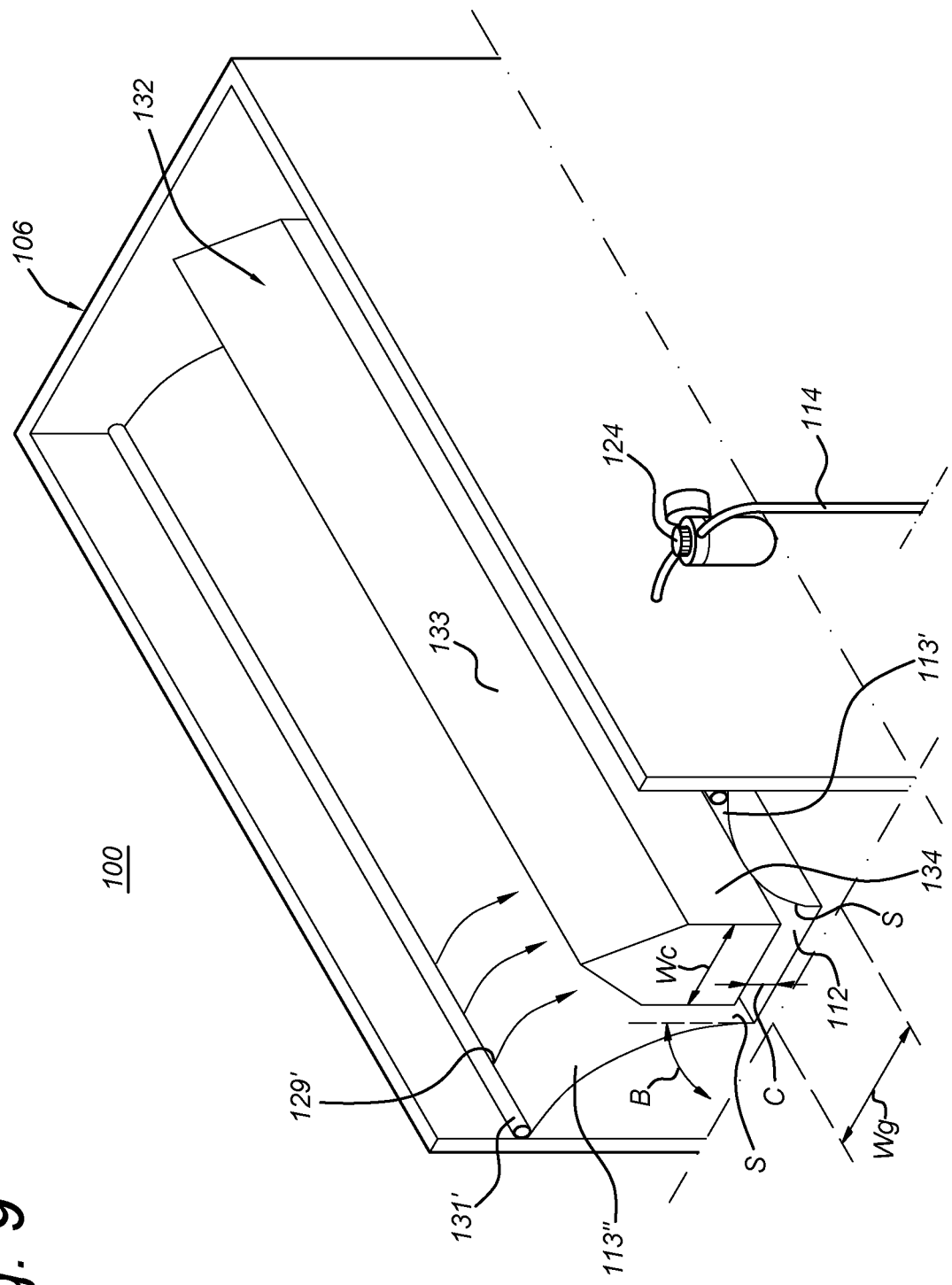

FIG. 9 depicts a live insect larvae transport device 100 comprising an elongated cover member 132 arranged over and along a fluid guiding unit 112 according to an embodiment of the present invention.

In the embodiment shown, the live insect larvae transport device 100 may be considered to be the same as the one shown in FIG. 8 but wherein a cover member 132 is provided that extends above and along the fluid guiding unit 112 at a clearance distance "C", thus wherein the cover member 132 extends along and above the at least one fluid guiding members 12', 12", 12''' at a clearance distance "C" with respect thereto. The clearance distance "C" is sufficiently large to allow the first laminar flow of air with live insects, e.g. larvae, to flow freely over the top surface of each of the at least one fluid guiding member 12', 12", 12''' extending underneath the cover member 132.

The cover member 132 prevents that the first laminar flow over the fluid guiding unit 112, i.e. the at least one fluid guiding member 12', 12", 12''', drags too much conditioned air toward the exit of the live insect larvae transport device 100 at a proximal end thereof. In case too much air is being dragged along with the first laminar flow, then this would produce too much turbulence at the exit because of the limited flow capacity there through causing air being lifted upward at the proximal end of the live insect larvae transport device 100.

Therefore, the cover member 132 maintains homogenous distribution of conditioned air around the insect eggs in the at least one reservoir 128, 128' by minimizing the amount of conditioned air being dragged away and/or downward therefrom along with the first laminar flow over the fluid guiding unit 112.

In an embodiment, the cover member 132 has a height such that it extends and remains underneath the at least one reservoir 128, 128', so that conditioned air around the insect eggs is prevented from being dragged with the first laminar flow over the fluid guiding unit 112.

In another embodiment, the cover member 132 may further comprise a sloped roof 133 to prevent that live insects collect on the cover member 132 when dropping from the at least one reservoir 128, 128' onto the cover member 132, thereby ensuring that the live insects reach the first laminar flow of gas over the fluid guiding unit 112.

In a further embodiment, the cover member 132 comprises a plurality of cover side walls 134, e.g. oppositely arranged cover side walls 134, wherein each cover side wall 134 extends in upward and longitudinal/lengthwise direction along one of the convex side walls 113',113" to further reduce any suction or dragging of conditioned air by the first laminar air flowing over the fluid guiding unit 112. Note that lowest edges of each cover side wall 134 are arranged above the fluid guiding member 112 at the aforementioned clearance distance C. In a further embodiment, the cover member 132 comprises a bottom side (not visible in FIG. 9) which may be an open or a closed bottom side. In case the bottom side is closed, then the bottom side extends along and above the fluid guiding unit 112 at the aforementioned clearance distance C.

In an exemplary embodiment, the cover member 132 has a width $w_c$ which may be substantially the same as a width $W_g$ of the fluid guiding unit 112. Since the cover member 132 is arranged above the fluid guiding unit 112 at the clearance distance C, a slit "S" is provided between the cover member 132 and each of the convex side walls 113', 113". These slits S still allow discharged air from the second fluid discharge members 131, 131' to flow in laminar fashion over the convex side walls 113', 113" and pass through these slits S toward each of the at least one fluid guiding members 12', 12", 12'".

In an exemplary embodiment, the cover member 132 may have a height between 10 to 10 cm, e.g. 20 cm, and a width $W_c$ of 3 to 7 cm, e.g. 5 cm.

As mentioned earlier, the at least one reservoir 128, 128' comprising live insects, e.g. insect eggs, are to be maintained at a controlled and predetermined temperature and relative air humidity to stimulate and facilitate optimal hatching such that optimal release of live insects from the at least one reservoir 128, 128' reservoirs into the live insect receiving portion is achieved.

Figure 10:
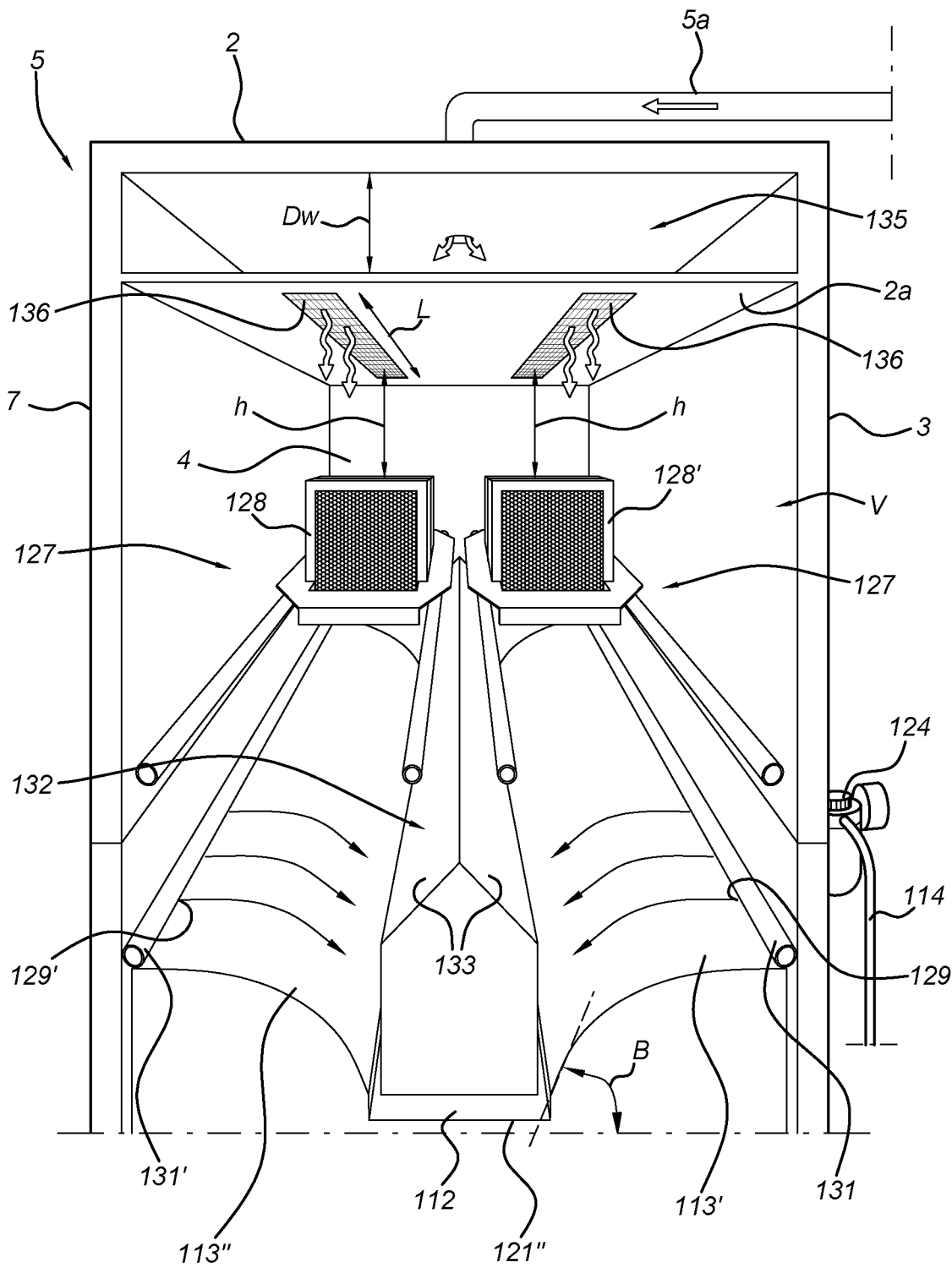
FIG. 10 shows a casing 5 of a live insect larvae transport device 100 according to an embodiment of the present invention.

To provide optimal temperature and relative humidity condition, FIG. 10 shows a casing 5 of a live insect larvae transport device 100 according to an embodiment of the present invention. In the depicted embodiment, the a live insect larvae transport device 100 comprises a casing 5 covering the fluid guiding unit 112 in the inners side of the casing 5, the flat or convex side walls 113', 113", and the feeder arrangement 127 in which the at least one reservoirs 128, 128' are received. The casing 5 comprises a top wall 2 and side walls 3, 4, 7 defining the inner side, and in particular a closed inner space or volume "V" in which the temperature is controllable as well as the relative humidity to provide an environment for the at least one reservoir 128, 128' to stimulate and facilitate optimal hatching. In order to provide air of a particular temperature and/or relative humidity, the live insect larvae transport device 100 further comprises an air feed channel 5a connected to the top wall 2 of the casing 5 for providing air of a desired temperature and/or relative humidity to the inner side of the casing 5 and in particular to the inner volume V.

In an embodiment, the casing 5 may be provided with a secondary top wall 2a arranged below the top wall 2 at wall distance $D_w$ therefrom such that a cavity space 135 is defined between the top wall 2 and secondary top wall 2a. The secondary top wall 2a further comprises one or more slits 136 such that air from the air feed conduit 5a entering the cavity/buffer space 135 is able to flow toward the inner volume V. That is, the one or more slits 136 fluidly connect the cavity/buffer space 135 and the inner volume V of the casing 5. The one or more slits 136 provided in the secondary top wall 2a allow air, e.g. temperature and/or humidity controlled air, to be provided to the inner volume V in distributed fashion so as to minimize turbulence in the inner volume. Therefore, the cavity space 135 in conjunction with the one or more slits 136 allow air from the air feed conduit 5a to enter the inner volume V with maximum homogeneity.

In an embodiment, the one or more slits 136 are arranged in longitudinal fashion, i.e. in a lengthwise direction "L" as depicted, thereby providing conditioned air in homogenous fashion along the fluid guiding unit 112. In an exemplary embodiment, each of the one or more slits 136 extends along 70% to 90%, e.g. 80%, of a length of the first laminar flow of gas, e.g. air, over the top surface of the at least one fluid guiding member 12', 12", 12'". In an exemplary embodiment, each of the one more slits 136 has a length between 50 to 100 cm, e.g. 60, 65, 70 cm. In a further exemplary embodiment, each of the one or more slits 136 has a width of about 3 cm to 6 cm, e.g. 4 cm or 5 cm, to further facilitate homogenous distribution of conditioned air entering the inner volume V of the casing 5.

In an advantageous embodiment, the one or more slits 136 extend above the at least one reservoir 128, 128' containing the live insects, e.g. insect eggs, for which conditioned air is to be provided for optimized hatching.

In another embodiment, each of the one or more slits 136 comprises a plurality of perforations covering 40% to 60%, e.g. 50%, of a surface area of the slit 136. In further embodiments each of the perforations is a substantially circular perforation having a diameter of about 4, 5, or 6 mm for example.

In an embodiment, the secondary top wall 2a with the one or more slits 136 is arranged above the at least one reservoir 128, 128' at a height of 5 to 15 cm, e.g. 10 cm to provide the conditioned air to the at least one reservoir 128. 128'.

Figure 1A:
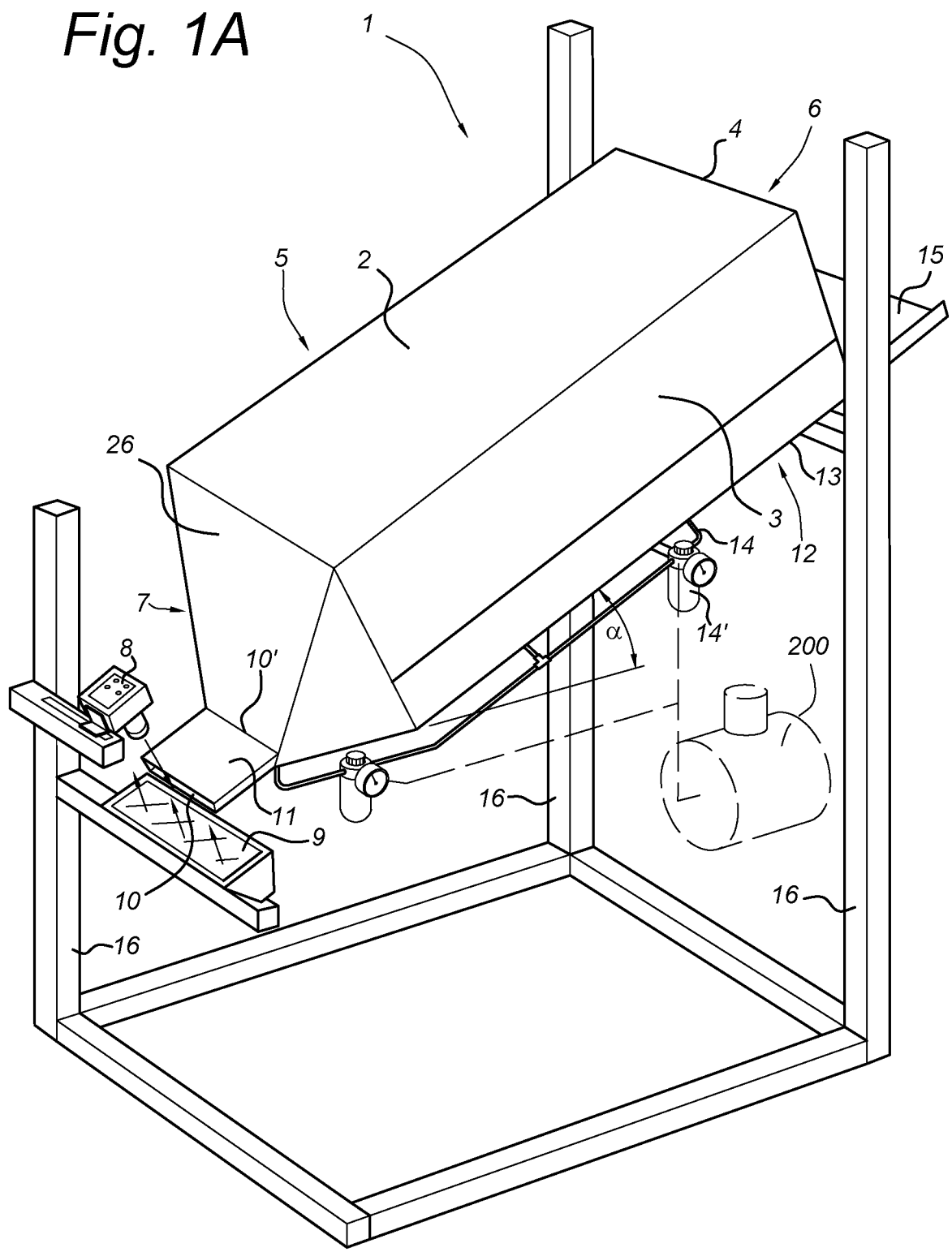
Figure 1B:
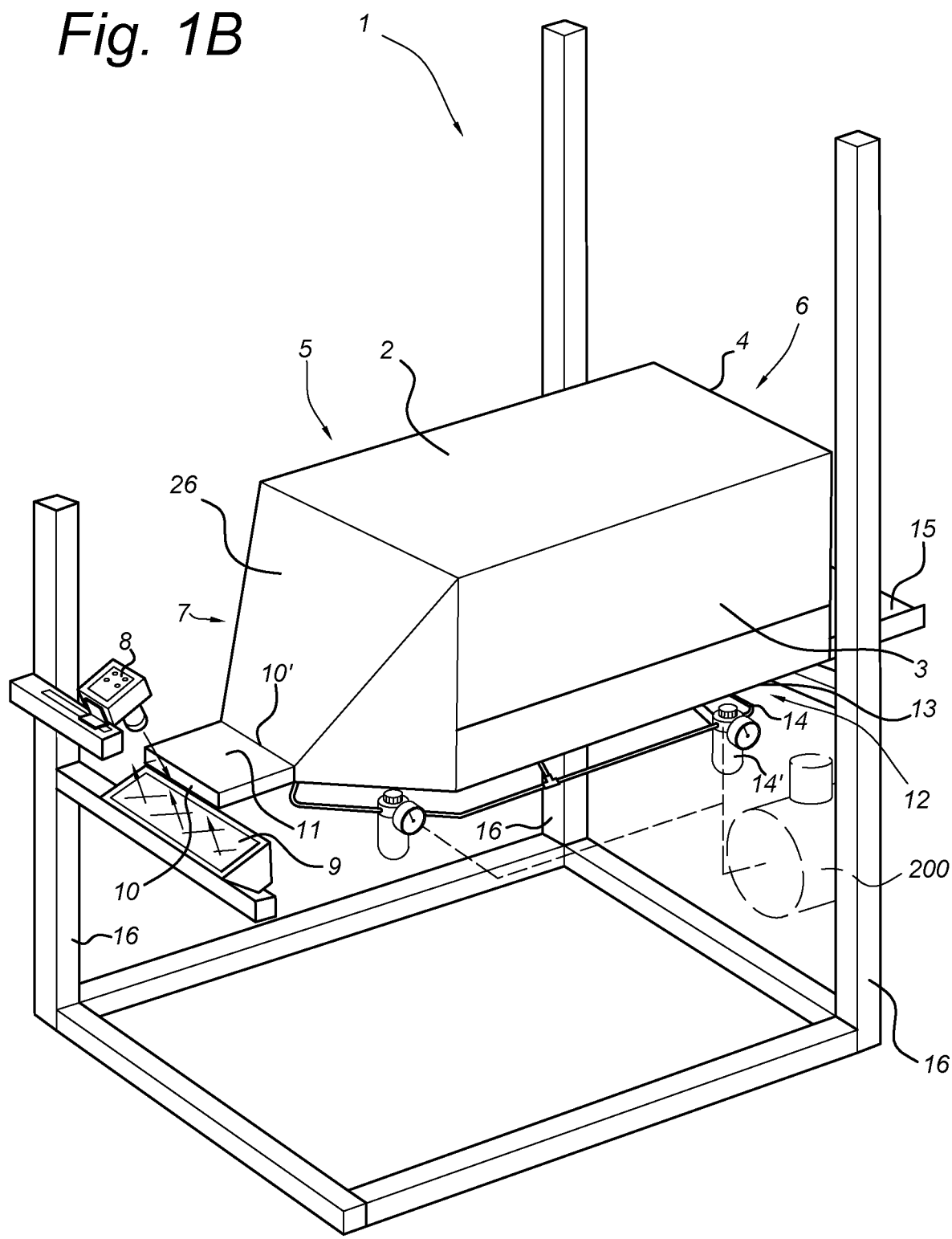

As mentioned earlier, the live insect larvae transport device 100 according to the present invention may comprise a live insects counting device 8, e.g. a camera, for counting live insects in the first laminar flow exiting the live insect larvae transport device 100 at the proximal end of the live insect discharge member 11 as shown in FIGS. 1A, 1B, and 2. In one embodiment, the live insects discharge member 11 may be a funnel shaped discharge member 11, e.g. having a rectangular cross section, configured to provide a narrow stream of fluid for accurate counting of the live insects exiting the live insect larvae transport device 100.

Figure 11:
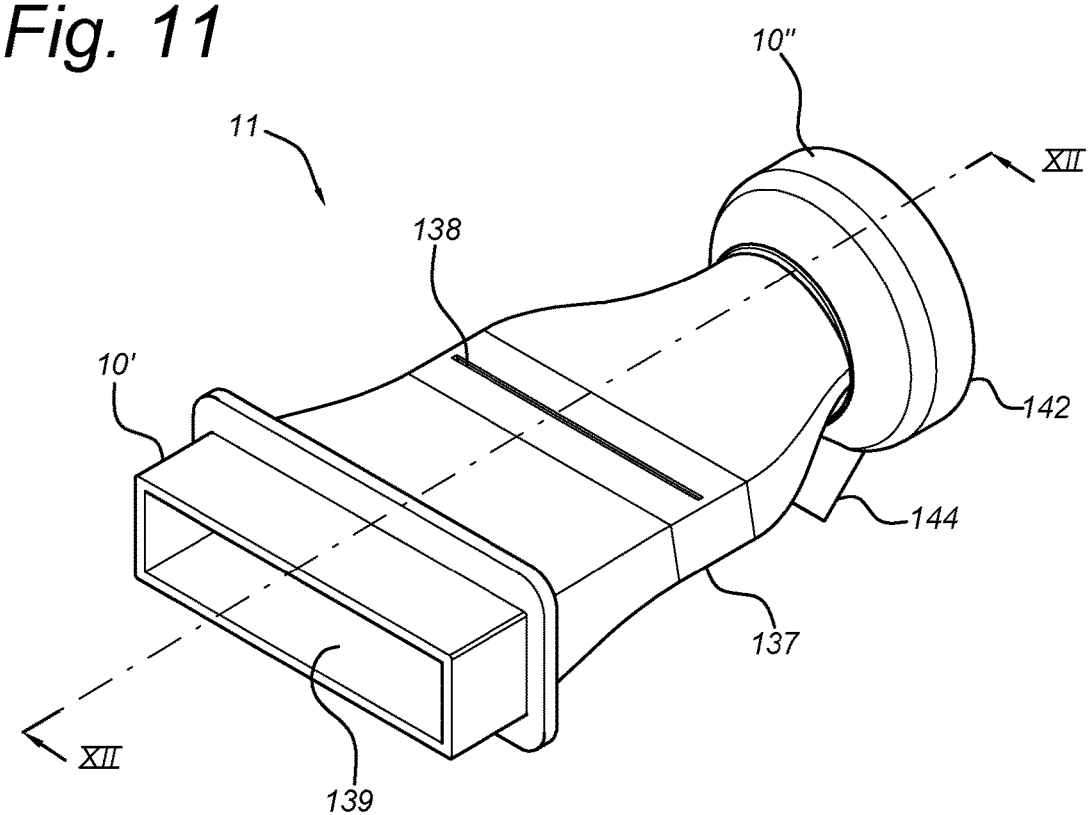
FIG. 11 shows a three dimensional view of a live insect discharge member 11 according to an embodiment of the present invention.

To further improve upon the accuracy and reliability of counting live insects exiting the live insect larvae transport device 100, further embodiments of the live insects discharge member 11 as discussed earlier are conceivable. For example, FIG. 11 shows a three dimensional view of a live insect discharge member 11 and FIG. 12 shows a cross sectional view of the live insect discharge member 11 according to an embodiment of the present invention.

In the depicted embodiments, the live insect discharge member 11 may comprise a throat portion 137 arranged between the distal end 10', i.e. the first end, and a proximal end 10", i.e. the second end, of the live insect discharge member 11. That it, a discharge channel 139 of the live insect discharge member 11 extends between the distal end 10' and proximal end 10" thereof and comprises a constricted or choked channel portion 140 at the throat portion 137. Here, the distal/first end 10' is configured for connection to the live insect larvae transport device 100 such that live insects exiting the transport device 100 can travel through the discharge channel 139 by entering at the distal/first end 10' and exiting from the proximal/second end 10".

As shown, the throat portion 137 is provided with a through hole 138, e.g. shaped as a (elongated) slit 138, laterally/sideways extending through the throat portion 137. The through hole/slit 138 allows the counting device 3, e.g. a camera, to be arranged next to the slit shaped through hole 138 and have a field of view into the discharge channel 139, in particular the constricted channel portion 140, for counting the number of live insects passing through the live insect discharge member 11 as they exit the live insect larvae transport device 100.

The advantage of having the slit shaped through hole 138 at the constricted channel portion 140 is that a pressure drop in the constricted channel portion 140 will develop according to the Venturi effect or Venturi principle. That is, the constricted channel portion 140 induces a Venturi effect allowing outside air "A" to be drawn/sucked into the constricted channel portion 140 via the slit shaped through hole 138 when an air stream carrying live insects flows through the discharge channel 139. As a result, suction at the slit shaped through hole 138 allows live insects to be counted by the counting device 3 whilst preventing that live insects escape the live insect discharge member 11 via the slit shaped through hole 138.

For improved operation of the counting device 8, e.g. a camera, a light source such as a lamp 9 may be provided as mentioned earlier with reference to FIG. 1A, 1B. To improve operation of the counting device 8, FIG. 12 shows an embodiment of a light source 9 such as an elongated lamp arranged next to and extending along the slit shaped through hole 138 on an opposite side of the live insect discharge member 11 with respect to the counting device 8. In particular, the counting device 8 is arranged on a first side $S_1$ whereas the light source 9 is arranged on an opposing second side $S_2$ of the live insect discharge member 11. Light from the light source 9 is able to pass through the slit shaped through hole 138 and reach the counting device 8. The constricted channel portion 140 then prevents live insects escaping through the slit shaped through hole 138 by virtue of the suction effect explained above when an air stream carrying live insects passes through the discharge channel 139.

Note that suction at the slit shaped through hole 138 allows the counting device 3 to be arranged on both sides $S_1$, $S_2$, e.g. above or below, the live insect discharge channel 11 and the light source 9 may then be arranged below or above the live insect discharge channel 11 respectively. In any case, the constricted channel portion 140 prevents live insects escaping via the slit shaped through hole 138 on both sides $S_1$, $S_2$ of the live insect discharge member 11. Since live insects cannot escape though the slit shaped through hole 138, contamination of the counting device 8 and/or light source 9 is eliminated, allowing the counting device 8 and light source 9 to be placed on either side $S_1$, $S_2$ of the live insect discharge member 11 whilst still allowing accurate counting of the number of live insects exiting the live insect larvae transport device 100.

As shown in FIGS. 11 and 12, in an embodiment the constricted channel portion 140 comprises a rectangular cross section, which allows a relatively narrow and elongated air stream of live insect to pass through the constricted channel portion 140 so that the counting device 8 is able to count the number of live insects much more accurately with a minimal number of uncounted live insects, which could have been be blocked by another live insect in the field of view of the counting device 8.

To obtain a most optimal field of view into the constricted channel portion 140, an embodiment is provided wherein the slit shaped through hole 138 has a length of at least 90% percent of a width of the constricted channel portion 140 in the lateral direction of the slit shaped through hole 138. This embodiment minimizes the number of live insects that could potentially bypass the field of view of the counting device 8.

In an embodiment, the slit shaped through hole 138 comprises a chamfered or rounded downstream inner edge 141, i.e. extending in the lengthwise direction of the slit shaped through hole 138 on a downstream side thereof, thereby reducing turbulence and maintaining laminar flow within the constricted channel portion 140 when air A is being drawn into the constricted channel portion 140 in the direction of air flowing from the first end 10' to the second end 10".

The live insect discharge member 11 with the slit shaped through hole 138 enabling a field of view into the constricted channel portion 140 allows for an extremely useful counting device 8 which is able to accurately count the number of live insects exiting the live insect larvae transport device 100. In particular, because accurate counting of live insects is now possible by means of the live insect discharge member 11, information on hatch and development characteristics of live insects in the live insect larvae transport device 100 can be deduced. For example, by counting the number live insects passing the live insect discharge member 11 it is possible to deduce what the effects are of temperature and/or relative humidity on live insects (e.g. insect eggs) and their hatch time in the at least one reservoir 128. Therefore, the live insect discharge member 11 and counting device 8 allow for gaining further information on live insect hatching characteristics.

Although the constricted channel portion 140 prevents live insect escaping though the slit shaped though bore 138, an outgoing air stream $A_o$ with live insects exiting the live insect discharge member 11 at its proximal/second end 10" is generally slower than an incoming air stream $A_i$ entering the distal/first end 10'. To compensate for this loss of speed, an embodiment is provided wherein the proximal/second end 10" of the live insect discharge member 11 is provided with an air amplifier unit 142 which is configured to inject further air $A_f$ into the second end 10" of the live insect discharge member 11. This ensures that an outgoing air stream $A_o$ with live insects has sufficient speed and momentum to flow to other parts of a system, such as a cyclone separation system, connected to the second end 10" of the live insect discharge member 11.

In an exemplary embodiment, the air amplifier unit 142 comprises a circumferential chamber 143 fluidly coupled to an air feed connection 144 for connection to an air feed allowing further air $A_f$ to be injected into the proximal second end 10" of the live insect discharge member 11, and wherein one or more air amplifier outlets 145 are circumferentially arranged in an inner wall 147 of the second end 10" of the live insect discharge member 11 and wherein the one or more air amplifier outlets 145 are fluidly connected to the circumferential chamber 143. In this embodiment, the one or more air amplifier outlets 145 allow for an even injection of the further air $A_f$ into the second end 10" such that turbulence is minimised. In an exemplary embodiment, a single air amplifier outlet 145 may be provided in the form of a circumferential slit in the inner wall 147 fluidly coupled to the circumferential chamber 143, allowing for even injecting of further $A_f$.

As mentioned above, the air amplifier unit 142 allows for an outgoing air stream $A_o$ with live insects which has sufficient speed and momentum to flow to other parts of a system, such as a cyclone separator, connected to the second end 10" of the live insect discharge member 11.

FIG. 13 shows a cross sectional view of such a cyclone separation system 148 connected to one or more live insect larvae transport devices 100 according to an embodiment of the present invention. In the embodiment shown, the transport device 100 comprises the live insect discharge member 11 described earlier, e.g. comprising the throat portion 137 with the slit shaped through hole 138 and the constricted channel portion 140 to prevent live insects escaping there through by virtue of the Venturi effect. A counting device 8 may be provided next to the slit shaped through hole 138, possibly with a light source 9 such as a lamp on an opposite side of the throat portion 137. The slit shaped through hole 138 allows the counting device 8 to have a field of view into the constricted channel portion 140 for counting live insects passing through the live insect discharge member 11. The light source 9 is able to provide additional illumination through the slit shaped through hole 138.

As depicted, a cyclone separation system 148 is connected to one or more live insect larvae transport devices 100 to separate live insects from an outgoing air stream $A_o$ of each live insect discharge member 11. The cyclone separation system 148 comprises a main cyclone chamber 149 having a top chamber part 150 and a conical shaped bottom chamber part 151, wherein the top chamber part 150 is connected to one or more intake channels 152 each of which is arranged for connection to a primary air source providing an air stream comprising live insects. Here, the air stream provided by the primary air source is an outgoing air stream $A_o$ of a live insect discharge member 11 as described above. Therefore, each of the one or more intake channels 152 is arranged for connection to a live insect larvae transport device 100 of the one or more live insect larvae transport devices 100.

Note that only one live insect larvae transport device 100 is depicted for clarity purposes and the skilled person will understand the each of the depicted first ends 10' of the live insect discharge members 11 is connected to a live insect larvae transport device 100.

The bottom chamber part 151 is connected to a discharge nozzle 153 comprising a discharge end 153' having a main discharge conduit (not shown) for discharging the live insects from the cyclone separation system 148. The discharge end 153' comprises an air injection member 154 for connection to a secondary air source 155 and wherein the air injection member 154 is configured to inject air back into the discharge nozzle 153. Injecting air back into the discharge nozzle 153 stops the discharge of live insects.

In an advantageous embodiment, the air injection member 154 is configured for intermittent air injection back into the discharge nozzle 153.

Each of the one or more live insect larvae transport devices 100 provides an outgoing air stream $A_o$ with live insects passing through a live insect discharge member 11 toward the cyclone separation system 148, which subsequently discharges separated live insects in batch wise fashion by intermitted operation of the air injection member 154.

As the skilled person will understand, in operation the one or more intake channels 152 carrying the outgoing air streams $A_o$ induce a main vortex in the top chamber part 150 allowing centrifugal separation of the live insects from the combined outgoing air streams $A_o$ in the top chamber part 150. The separated live insects follow a conical inner wall of the bottom chamber part 151 toward the discharge nozzle 153. Due to the conical shaped bottom chamber part 151, an ascending inner vortex of "clean" air is generated that exits the top chamber part 150 through an air exit $E_A$ arrange thereon.

Discharged live insects may be collected in a container 156 arranged underneath the discharge nozzle 153 and wherein the container 156 is movable by means of a conveyor system 157. For example, in case the container 156 contains a desired number of live insects, then the air injection member 154 may be activated to inject air back into the discharge nozzle 153 as a result of which discharge of live insects is temporarily stopped. As the discharge of live insects has stopped, the container 156 may be replaced with another container, and once the other container has been correctly positioned, the air injection member 154 may be deactivated to resume discharge of separated live insects from the cyclone separation system 148.

In an embodiment, the cyclone separation system 148 may comprise a further counting device 158, e.g. a further camera, arranged next to the discharge nozzle 153 for counting the number of live insects being discharged therefrom. Activation and deactivation of the air injection member 154 may be controlled based on the counted number of live insects being discharged. Optionally, a further light source 159 may be provided to improve illumination conditions for the further counting device 158.

As further shown, the second end 10'' of each live insect discharge member 11 may be provided with an air amplifier unit 142 to boost the outgoing air stream $A_o$ such that it attains sufficient speed and momentum.

Advantageously, a plurality of live insect larvae transport devices 100 are connected to a corresponding number of intake channels 152 so that the cyclone separation system 148 may operate continuously without interruption to the flow of live insects entering the cyclone separation system 148. In this way the cyclone separation system 148 can be scaled up to achieve batch wise discharge of any desired number of live insects. Note that the top chamber part 150 may be connected to an auxiliary intake channel 160 configured to provide a "pilot" air stream into the top chamber part 150 to further optimize centrifugal separation of the live insects entering the main cyclone body 149.

These embodiments of live insect transport devices of the invention are all suitable for transportation of live neonate larvae of the black soldier fly, which larvae have a body diameter of between 1 mm and 4 mm and a body length which ranges between 5 mm and 12 mm.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims.

The invention claimed is:

1. A live insect larvae transport device comprising:
a fluid guiding unit comprising a distal end and a proximal end, and at least one longitudinal fluid guiding member comprising a distal end and a proximal end, wherein the distal end of the fluid guiding member is arranged at the distal end of the fluid guiding unit and wherein the proximal end of the fluid guiding member is directed toward the proximal end of the fluid guiding unit,
wherein the at least one fluid guiding member further comprises a smooth top surface extending from the distal end to the proximal end of the fluid guiding member, the top surface comprising a live insect larvae receiving portion between the distal end and proximal end of the at least one fluid guiding member, and wherein the fluid guiding member is tilted at an angle (α) relative to the horizontal;
a first fluid discharge member located at the distal end of the fluid guiding unit and being configured to connect to a source of fluid, wherein the first fluid discharge member is further configured to provide a relative humidity-controlled first laminar flow of gas over the top surface of the at least one fluid guiding member from the distal end to the proximal end thereof during operation of the transport device; and wherein the transport device further comprises
a feeder arrangement located above the live insect larvae receiving portion of the top surface of the fluid guiding unit, wherein the feeder arrangement is configured to receive at least one reservoir for hatching live insect larvae at a predetermined distance above the live insects receiving portion of the top surface and releasing hatched live insect larvae from the at least one reservoir above the live insect larvae receiving portion into the relative humidity-controlled first laminar flow of gas, wherein the live insect larvae transport device further comprises a casing covering the fluid guiding unit and wherein the feeder arrangement further comprises a unit for controlling relative air humidity at the inner side of the casing.

2. The live insect larvae transport device according to claim 1, wherein the at least one fluid guiding member has a length in the longitudinal direction of between 10 cm and 200 cm, preferably between 20 cm and 140 cm, more preferably between 25 cm and 120 cm, most preferably about 25 cm to 50 cm.

3. The live insect larvae transport device according to claim 1, wherein said transport device comprises at least two imbricatedly coupled longitudinal fluid guiding members, the fluid guiding members being imbricatedly coupled with a coupler located at the proximal end of a first fluid guiding member and the distal end of a second fluid guiding member.

4. The live insect larvae transport device according to claim 3, wherein the coupler imbricatedly coupling the at least two fluid guiding members is provided with a further fluid discharge member comprising a connector configured to connect each further fluid discharge member to a source of gas, and wherein the further fluid discharge member(s) is/are configured to reinforce from below the first laminar flow of gas over the top surface of the at least one fluid guiding member from the distal end to the proximal end of the fluid guiding unit during operation of the transport device.

5. The live insect larvae transport device according to claim 4, wherein the source of gas comprises a compressor providing compressed gas and/or a pump for driving gas through the fluid discharge member.

6. The live insect larvae transport device according to claim 1, wherein the gas is temperature-controlled gas.

7. The live insect larvae transport device according to claim 1, wherein the tilt angle ($\alpha$) is between 0° and 45°.

8. The live insect larvae transport device according to claim 1, further comprising a live insect discharge member comprising a flat surface with a first end and a second end, the first end being coupled to the proximal end of the fluid guiding unit.

9. The live insect larvae transport device according to claim 8, further comprising a live insects counting device for counting live insects in the first laminar flow exiting the live insect transport device at the proximal end of the live insect discharge unit.

10. The live insect larvae transport device according to claim 1, wherein the reservoir for live insects is an insect egg collection interface or an insect egg holder.

11. The live insect larvae transport device according to claim 1, wherein the feeder arrangement is configured to receive between 2 and 250 reservoirs for releasing live insect larvae above the live insects receiving portion and/or the feeder arrangement is configured to receive the at least one reservoir in a predetermined orientation relative to the direction of the path for the first laminar flow of gas, such that a major surface of the reservoir(s) is oriented perpendicular to the direction of said first laminar flow of gas.

12. The live insect larvae transport device according to claim 1, wherein the live insects receiving portion further comprises side walls located along longitudinal sides of the at least one longitudinal fluid guiding member, the side walls being tilted at an obtuse angle ($\beta$) relative to the top surface of the at least one fluid guiding member, wherein each side wall having a top side and a bottom side, the bottom side being connected to a longitudinal side of the at least one longitudinal fluid guiding member, and a smooth surface arranged between the bottom side and the top side, and wherein the top side of each side wall is provided with at least a second fluid discharge member, each second fluid discharge member being located at the top side of each side wall and comprising a connector configured to connect the second fluid discharge member to a source of gas, for providing a second laminar flow of gas over the surface of the side walls from the top side of the side walls to the path of the first laminar flow of gas during operation of the transport device, and wherein the second laminar flow of gas is oriented perpendicular to the first laminar flow of gas; or wherein the live insects receiving portion further comprises convex side walls located along longitudinal sides of the at least one longitudinal fluid guiding member, wherein each convex side wall has a top side and a bottom side and a smooth convex surface arranged between the top and bottom side, the bottom side being connected to a longitudinal side of the at least one fluid guiding member, and wherein the top side of each convex side wall is provided with a second fluid discharge member comprising a connector configured to connect the second fluid discharge member to a source of gas for providing a second laminar flow of gas over the surface of the convex side wall from the top side thereof to the at least one fluid guiding member during operation of the live insect larvae transport device.

13. The live insect larvae transport device according to claim 12, further comprising a cover member extending along and above the at least one fluid guiding member at a clearance distance (C) with respect thereto, wherein the cover member preferably comprises a plurality of cover side walls, wherein each cover side wall extends in upward and longitudinal/lengthwise direction along one of the convex side walls, and/or wherein the cover member further comprises a sloped roof.

14. The live insect larvae transport device according to claim 1, wherein the casing covering the fluid guiding unit and the feeder arrangement comprises a top wall and side walls defining a closed inner volume in which the at least one reservoir is arranged, and wherein the live insect larvae transport device comprises an air feed channel connected to the top wall configured to provide air of a desired temperature and/or relative humidity to the inner volume of the casing, and wherein the casing preferably further comprises a secondary top wall arranged below the top wall at a distance therefrom defining a cavity space between the top wall and the secondary top wall, wherein the secondary top wall further comprises one or more slits fluidly connecting the cavity space and the inner volume of the casing.

15. The live insect larvae transport device according to claim 1, wherein the live insect discharge member comprises a throat portion arranged between the first end and the second end of the live insect discharge member, wherein a discharge channel extends between the first end and the second end and comprises a constricted channel portion at the throat portion, and wherein the throat portion is provided with a slit shaped through hole laterally extending through the throat portion, and wherein the constricted channel portion preferably comprises a rectangular cross section.

16. The live insect larvae transport device according to claim 15, wherein the slit shaped through hole has a length of at least 90% percent of a width of the constricted channel portion in a direction of the slit shaped through hole, and wherein the slit shaped through hole preferably comprises a chamfered or rounded downstream inner edge.

17. The live insect larvae transport device according to claim 15, wherein the second end of the live insect discharge member is provided with an air amplifier unit which is configured to inject further air into the second end.

18. A combination of a cyclone separation system and one or more live insect larvae transport devices according to claim 1, wherein the cyclone separation system comprises a main cyclone chamber having a top chamber part and a conical shaped bottom chamber part, wherein the top chamber part is connected to one or more intake channels each of which is arranged for connection to a live insect larvae transport device of the one or more live insect larvae transport devices, and wherein the bottom chamber part is connected to a discharge nozzle comprising a discharge end having a main discharge conduit for discharging live insects from the cyclone separation system, and wherein the discharge end comprises an air injection member for connection to a secondary air source and wherein the air injection member is configured to inject air back into the discharge nozzle.

19. The combination according to claim 18, wherein the cyclone separation system comprises a further counting device arranged next to the discharge nozzle for counting the number of live insects being discharged therefrom.

20. A method for transporting live neonate insect larvae comprising the steps of:

providing an ovisite comprising insect eggs;

providing a live insect larvae transport device according to claim 1;

providing a laminar flow of air in the transport device;

placing said ovisite in a feeder arrangement of said transport device; and transporting live neonate insect larvae upon hatching of said larvae in the ovisite and dropping down therefrom into the first laminar flow of air.

21. The method according to claim 20 wherein the insect is black soldier fly.

22. The method according to claim 20, wherein the air in the first laminar flow is temperature controlled air at a temperature of between 22° C. and 30° C. and/or is relative-humidity controlled air with a relative humidity of between 40% and 90%, and/or the air in the first laminar flow has a speed of between 10 m/sec and 70 m/sec and/or has a pressure at the location of the fluid discharge member of between 10 bar and 0.8 bar.

* * * * *